(12) United States Patent
Hunter

(10) Patent No.: US 8,633,031 B2
(45) Date of Patent: Jan. 21, 2014

(54) EXPRESSION QUANTIFICATION USING MASS SPECTROMETRY

(75) Inventor: Christine L. Hunter, San Mateo, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 749 days.

(21) Appl. No.: 12/571,005

(22) Filed: Sep. 30, 2009

(65) Prior Publication Data
US 2010/0227352 A1  Sep. 9, 2010

Related U.S. Application Data

(63) Continuation of application No. 11/441,457, filed on May 25, 2006, now abandoned, which is a continuation-in-part of application No. 11/134,850, filed on May 19, 2005, now abandoned.

(60) Provisional application No. 60/572,826, filed on May 19, 2004.

(51) Int. Cl.
G01N 33/00 (2006.01)
B01D 59/44 (2006.01)

(52) U.S. Cl.
USPC .......................................... 436/86; 250/282

(58) Field of Classification Search
USPC .......................................... 436/86; 250/282
See application file for complete search history.

(56) References Cited

U.S. PATENT DOCUMENTS

| | | | |
|---|---|---|---|
| 5,075,547 A | 12/1991 | Johnson et al. | |
| 5,854,084 A | 12/1998 | Drukier et al. | 436/541 |
| 6,011,259 A | 1/2000 | Whitehouse et al. | |
| 6,358,996 B1 | 3/2002 | Alexander et al. | |
| 6,432,639 B1 | 8/2002 | Lichter et al. | |
| 6,475,807 B1 | 11/2002 | Geysen et al. | |
| 6,635,452 B1 | 10/2003 | Monforte et al. | |
| 6,670,194 B1 | 12/2003 | Aebersold et al. | |
| 6,852,544 B2 | 2/2005 | Aebersold et al. | |
| 7,105,806 B2 | 9/2006 | Pappin et al. | |
| 7,148,069 B2 | 12/2006 | Miyano et al. | |
| 7,195,751 B2 | 3/2007 | Pappin et al. | |
| 7,307,169 B2 | 12/2007 | Pappin et al. | |
| 7,309,858 B2 | 12/2007 | Pappin et al. | |
| 7,355,045 B2 | 4/2008 | Dey et al. | |
| 2002/0030159 A1 | 3/2002 | Chernushevich et al. | |
| 2002/0037532 A1 | 3/2002 | Regnier et al. | |
| 2002/0076739 A1 | 6/2002 | Aebersold et al. | |
| 2002/0192720 A1 | 12/2002 | Parker et al. | |
| 2003/0092076 A1 | 5/2003 | Regnier et al. | |
| 2003/0124606 A1 | 7/2003 | Suckau et al. | |
| 2003/0194717 A1 | 10/2003 | Schmidt et al. | |
| 2003/0211622 A1 | 11/2003 | Roberts | |
| 2003/0213901 A1 | 11/2003 | Covey et al. | |
| 2004/0026612 A1 | 2/2004 | Bateman et al. | |
| 2004/0033625 A1 | 2/2004 | Aebersold | |
| 2004/0219685 A1 | 11/2004 | Pappin et al. | |
| 2004/0219686 A1 | 11/2004 | Pappin et al. | |
| 2004/0220412 A1 | 11/2004 | Pappin et al. | |
| 2005/0048489 A1 | 3/2005 | Thompson et al. | |
| 2005/0147982 A1 | 7/2005 | Pappin et al. | |
| 2005/0147985 A1 | 7/2005 | Pappin et al. | |
| 2005/0148087 A1 | 7/2005 | Pappin et al. | |
| 2005/0148771 A1 | 7/2005 | Dey et al. | |
| 2005/0148773 A1 | 7/2005 | Pappin et al. | |
| 2005/0148774 A1 | 7/2005 | Dey et al. | |
| 2005/0153456 A1 | 7/2005 | Pappin | |
| 2005/0196789 A1 | 9/2005 | Tomlinson et al. | |
| 2005/0208550 A1 | 9/2005 | Pappin et al. | |
| 2006/0073611 A1 | 4/2006 | Grainger | |
| 2006/0078960 A1 | 4/2006 | Hunter et al. | |
| 2006/0105416 A1 | 5/2006 | Pappin et al. | |
| 2006/0172319 A1 | 8/2006 | Yan et al. | |
| 2007/0023628 A1 | 2/2007 | Hamon et al. | |
| 2007/0054345 A1 | 3/2007 | Hunter | |
| 2007/0141659 A1 | 6/2007 | Pappin et al. | |
| 2007/0161116 A1 | 7/2007 | Copse | |
| 2008/0033662 A1 | 2/2008 | Pappin et al. | |
| 2008/0067347 A1 | 3/2008 | Pappin et al. | |
| 2008/0101989 A1 | 5/2008 | Pappin et al. | |

FOREIGN PATENT DOCUMENTS

| | | |
|---|---|---|
| JP | 2004-506900 | 3/2004 |
| WO | 9727331 | 7/1997 |
| WO | 9826095 | 6/1998 |

(Continued)

OTHER PUBLICATIONS

Thompson et al., "Tandem mass tags: a novel quantification strategy for comparative analysis of complex protein mixtures by MS/MS," Analytical Chemistry, 75:1895-1904 (2003).

Unwin et al., "Multiple reaction monitoring to identify sites of protein phosphorylation with high sensitivity", Mol Gell Proteomics, 4: 1134-44, 2005.

Lisek et al., "Quantitation of Endogenous Substance P by On-Line Microcolumn Liquid Chromatography/Continuous-flow Fast-atom Bombardment Mass Spectrometry," Rapid Communications in Mass Spectrometry, 3(2): 43-46, 1989.

(Continued)

*Primary Examiner* — Susan Hanley
*Assistant Examiner* — Paul Martin

(57) ABSTRACT

In various aspects, the present teachings provide systems, methods, assays and kits for the absolute quantitation of protein expression. In various aspects, the present teachings provide methods of determining the concentration of one or more proteins of interest in one or more samples of interest. In various aspects, the present teachings provide methods of determining the absolute concentration of one or more isoforms of a protein using standard samples of signature protein fragments and parent-daughter ion transition monitoring (PDITM). In various embodiments, the absolute concentration of multiple isoforms of a biomolecule in a sample, multiple proteins in a biological process, a combination of multiple samples, or combinations thereof, can be determined in a multiplex fashion using the present teachings. In various aspects, provided are methods of assessing the response of a biological system to a chemical agent.

20 Claims, 7 Drawing Sheets

(56) References Cited

FOREIGN PATENT DOCUMENTS

| WO | 0011208 | 3/2000 |
|---|---|---|
| WO | WO 02/14867 | 2/2002 |
| WO | 0229003 | 4/2002 |
| WO | 0248717 | 6/2002 |
| WO | 03025576 | 3/2003 |
| WO | 03056299 | 7/2003 |
| WO | 03069328 | 8/2003 |
| WO | 2004086050 | 10/2004 |
| WO | 2005012247 | 2/2005 |
| WO | 2005114700 | 12/2005 |
| WO | 2006017208 | 2/2006 |

OTHER PUBLICATIONS

Scrivener et al.,. "Peptidomics: A new approach to affinity protein microarrays," Proteomics, 3:122-128, 2003.
Anderson et al., "The Human Plasma Proteome", Molecular & Cellular Proteomics1.11, 1: 845-67, 2002.
Stemmann et al., "Dual Inhibition of Sister Chromatid Separation at Metaphase," Cell, 107: 715-726, 2001.
Wu et al., "An Automated MALDI Mass Spectrometry Approach for Optimizing Cyclosporin Extraction and Quarrtitation," Analytical Chemistry, 69(18): 3767-3771, 1997.
Labaer, "So, You Want to Look for Biomarkers (Introducation to the Special Biomarkers Issue)," Journal of Proteome Research, 4: 1053-1059, 2005.
"Applied Biosystems iTRAQ Reagents. Amine-Modifying Labeling Reagents for Multiplexed Relative and Absolute Protein Quantification," Chemistry Referenoe Guide, May 2004.
Ross et al, "Multiplexed Protein Quantification in *Saccharymyces cerevisiae* Using Amine-reactive Isobaric Tagging Reagents," Molecular & Cellular, 3: 1154-1169, 2004.
International Search Report, PCT/US2005/017799, date of mailing Nov. 11, 2006.
Anderson et al., "Mass Spectrometric Quantitation of Peptides arid Proteins Using Stable Isotope Standards and Capture by Anti-Peptide Antibodies (SISCAPA)", J. Proteome Res., 3(3): 235-44, 2004.
Bakhtiar, R. et al., "Mass Spectrometry of the Proteome" Mol Pharmacol. 60:405-415, 2001.
Feasley, C.L. et al., "Affinity Selection of Glycopeptides in Canine Immune-Mediated Arthritis" 52nd Conference of the American Society for Mass Spectrometry. May 24-27, 2004, Nashville, Tennessee (Abstract downloaded from ASMS Archives at httpl/www.asms.org/aspfolder/ASMSAbstracts.html).
Gartner C.G. et al., "Use of a Non-Cleavable Isotope-Labeled Biotin Reagent for the Determination of Relative Protein Expression Levels" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Grote J. et al., "Double-Detection Technology for Bioaffinity Studies" 52nd Conference of the American Society for Mass Spectrometry. May 24-27, 2004. Nashville, Tennessee (Abstract downloaded from ASMS Archives at http://www.asms.org/aspfolder/ASMSAbstracts.html).
Hahner, S. et al., "Label-free Quantitative Protein Analysis by LC-MALDI-TOF/TOF" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Haley, J. D. et al., "A Novel Fragment Ion Tag Approach to the Measurement of Tyrosine Kinase Signaling Pathways" 52nd Conference of the American Society for Mass Spectrometry. May 24-27, 2004, Nashville. Tennessee. (Abstract downloaded from ASMS Archives at http://www.asms.org/aspfolder/ASMSAbstracts.html).
Hwang, S. et al., "Quantitative Proteomic Analysis of Nuclear Proteins during Apoptosis using Stable Isotope Labeling" 52nd Conference of the American Society for Mass Spectrometry. May 24-27, 2004, Nashville, Tennessee (Abstract downloaded from ASMS Archives at http://www.asms.org/aspfolder/ASMSAbstracts.html).

Jedrzejewski, P.T. et al., "De Novo Sequencing of Protease Inhibitors from Libraries Following Affinity Selection Mass Spectrometry" 52nd Conference of the American Society for Mass Spectrometry. May 24-27, 2004, Nashville. Tennessee (Abstract downloaded from ASMS Archives at http://www.asms.org/aspfolder/ASMSAbstracts.html).
Liu, T. et al., "High Throughput Quantitative Proteome Analysis using Trypsin Catalyzed 18O Labeling, Thiol-Specific Enrichment, and Accurate Mass and Time Tags" 52nd Conference of the American Society for Mass Spectrometry, May 24-27, 2004, Nashville, Tennessee (Abstract downloaded from ASMS Archives at http://www.asms.org/aspfolder/ASMSAbstracts.html).
Lubeck, M. et al., "Differential Prateomics Based on LC MS(n) Data without Labeling" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Lucas, D.A. et al., "Quantitative Proteomic Analysis of Inorganic Phosphate-Induced MC3T3-E1 Osteoblast Cells" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Nisar, S. et. al., "Nanoelectrospray Ionization Tandem Mass Spectrometric Identification of Cytochrome P450s in Human Liver and Colorectal Metastases" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Qu, J. et al., "Determination of MPL Induced Tyrosine Aminotransferase Level Changes in Rat Liver Using Liquid Chromatography Tandem Mass Spectrometry and ICAT", 52nd Conference of the American Society for Mass Spectrometry, May 24-27, 2004. Nashville, Tennessee (Abstract downloaded from ASMS Archives at http://www.asms.org/aspfolder/ASMSAbstracts.html).
Ross, P. et al., "Relative and Absolute Quantitation in Yeast Proteomics using Multiplexed Isobaric Peptide Tags" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Schaefer, J. et al., "An Elegant Gel-Free Strategy for Quantitative Protein Profiling using Isotope Labeled PST Tags (qPST)" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Wang, G, et al., "Relative Quantification of Highly Complex Proteomes using Liquid Chromatography and Nano-Spray Tandem Mass Spectrometry" 52nd Conference of the American Society for Mass Spectrometry. May 24-27, 2004, Nashville, Tennessee (Abstract downloaded from ASMS Archives at http://www.asms.org/aspfolder/ASMSAbstracts.html).
Whitelegge, J.P. et al., "Can Isotope Ratio be Reliably Measured from Peptide Isotope Distributions for Stable-Isotope Coding in Proteomics" 52nd Conference of the American Society for Mass Spectrometry, May 24-27, 2004, Nashville, Tennessee (Abstract downloaded from ASMS Archives at http://www.asms.org/aspfolder/ASMSAbstracts.html).
Adkins, Joshua N. et al., "Toward a Human Blood Serum Proteome," Molecular & Cellular Proteomics, vol. 1:947-955 (2002).
Agrawal, Arun K. et al., "Constitutive and Inducible Hepatic Cytochrome P450 Isoforms in Senescent Male and Female Rats and Response to Low-Dose Phenobarbital," Drug Metabolism and Disposition. vol. 31(5):612-619 (2003).
Anderson, Leigh, "Candidate-based proteomics in the search for biomarkers of cardiovascular disease." J. Physiol., vol. 563(1):23-60 (2005).
Barnidge, David R. et al., "Absolute Quantification of the G Protein-Coupled Receptor Rhodopsin by LC/MS/MS Using Proteolysis Product Peptides and Synthetic Peptide Standards." Anal. Chem., vol. 75:445-451 (2003).
Craig, Robertson et al., "Open Source System for Analyzing, Validating, and Sorting Protein Identification Data," J. Proteome Res., vol. 3(6):1234-1242 (2004).

(56) References Cited

OTHER PUBLICATIONS

Gerber, Scott A. et al., "Absolute quantification of proteins end phosphoproteins from cell lysates by tandem MS," PNAS, vol. 100(12):6940-6945 (2003).

Hopp, Thomas P. et al., "Prediction of protein antigenic determinants from amino acid sequences," Proc. Natl. Acad. Sci. USA, vol. 78(6):3824-3828 (1981).

Hunter, Christie et al., "Using Stable Isotope Tags and a Hybrid Quadrupole-Linear Ion Trap Mass Spectrometer for Quantifying Proteins," Retrieved online: http://docs.appliedbiosystems.com/pebiodocs/00113938.pdf (2004).

Julka, Samir et al., "Quantification in Proteomics through Stable Isotope Coding: A Review," Journal of Proteome Research, vol. 3:350-383 (2004).

Krokhin, O.V. et al., "An Improved Model for Prediction of Retention Times of Tryptic Peptides in Ion Pair Reversed-phase HPLC," Molecular & Cellular Proteomics, vol. 3:908-919 (2004).

Kuhn. Eric et al., "Quantification of C-reactive protein in the serum of patients with rheumatoid arthritis using multiple reaction monitoring mass spectrometry and 13C-labeled peptide standards," Proteomics, vol. 4:1-12 (2004).

Zhang Fagen et al., "Quantitation of human glutathione S-transferases in complex matrices by liquid chromatography/tandem mass spectrometry with signature peptides," Rapid Communications in Mass Spectrometry, vol. 18:491-498 (2004).

Written Opinion of International Searching Authority, PCTUS2005/017799, date of mailing Nov. 1, 2006.

Alterman et al., "Qualitative and Quantitative: Maldi TOF-Based Proteomic Approach to the Profiling of Cytochrome P450 Isozymes," Poster No. 102, Mass Spectrometry in Systems Biology Keystone Symposium, Santa Fe, New Mexico, Feb. 15, 2004.

Applied Biosystems Cleavable ICAT® Reagent Kit for Protein Labeling, Protocol, Sep. 2003.

Applied Biosystems "Detection and Quantitation of Biomarkers / Peptides Using the Q TRAP® & 4000 Q TRAP® Systems", Feb. 25, 2004.

Applied Biosystems "Detection and Quantitation of Biomarkers / Peptides Using the Q TRAP® & 4000 Q TRAP® Systems", Mar. 18, 2004.

Applied Biosystems "Detection and Quantitation of Biomarkers / Peptides Using the Q TRAP® & 4000 Q TRAP® Systems", May 13, 2004.

Hunter, C., "Automated Protein Characterization and Quantitation using a 4000 QTRAP™ Hybrid Quadrupole—Linear Ion Trap Mass Spectrometer," Presentation at the 2004 San Diego Human Proteome Project: Plotting the Course for Proteomics Conference, Jan. 14-15, 2004.

Hunter, et al. "Using Stable Isotope Tags and a Hybrid Quadrupole-Linear Ion Trap Mass Spectrometer for Quantifying Proteins"; Poster No. M-434, Proc. $52^{nd}$ ASMS Conf. on Mass Spec. and Allied Topics, Nashville, TN May 23-27, 2004.

Hunter, et al. "Using Stable Isotope Tags and a Hybrid Quadrupole-Linear Ion Trap Mass Spectrometer for Quantifying Proteins"; Abstract submitted for Proc. $52^{nd}$ ASMS Conf. on Mass Spec. and Allied Topics, Abstract #570 available online Apr. 15, 2004.

Hunter et al., "Using Stable Isotope Tags and a Hybrid Quadrupole-Linear Ion Trap Mass Spectrometer for Quantifying Proteins," 6th Siena Meeting: From Genome to Proteome—Siena, Italy—Presentation and Abstract, Aug. 29-Sep. 2, 2004.

Hunter et al., "Using Stable Isotope Tags and a Hybrid Quadrupole-Linear Ion Trap Mass Spectrometer for Quantifying Cytochrome p450 Proteins," Poster No. 80, $21^{st}$ LC/MS Montreux Symposium, Switzerland, Nov. 10-12, 2004.

Hunter "Targeted Proteomic Techniques for Discovery and Quantitation of Post-Translationally Modified Proteins & Absolute Quantitation of Biomarkers," Australasian Proteomics Society Mtg, Presentation, Phillip Island, Australia, Feb. 4-6, 2005.

Hunter "Targeted Proteomic Techniques for Discovery and Quantitation of Post-Translationally Modified Proteins & Absolute Quantitation of Biomarkers," Lorne, Australia, Feb. 6, 2005.

Ong, S-E et al., "Mass spectrometry-based proteomics turns quantitative" *Nature Chem Biol* 1(5):252-262, Oct. 2005; online publication date Sep. 20, 2005.

Qu, et al. Improved Sensitivity for Quantification of Proteins using Triply Charged Cleavable Isotope-Coded Affinity Tag Peptides. *Rapid Commun. Mass Spect.* 19: 2857-64, Sep. 9, 2005.

Webb, et al., Protein Expression Profiling—Targeted Proteomic Techniques for Studying Cytochrome P450 Enzymes, Abstract, Human Proteome Organization 2nd Japan Conference; May 19-20, 2004.

Webb, et al., Protein Expression Profiling—Targeted Proteomic Techniques for Quantifying Cytochrome P450 Enzymes, Abstract, Human Proteome Organization 3rd Annual World Congress ; Beijing, China; Oct. 25-27, 2004.

USPTO issued Office Action mailed Nov. 21, 2006 in U.S. Appl. No. 11/134,850, filed May 19, 2005 entitled "Expression Quantification Using Mass Spectrometry;" Inventors: Hunter, et el.; Assignee: Applera Corporation.

USPTO issued Office Action mailed Oct. 5, 2007 in U.S. Appl. No. 11/134,850, filed May 19, 2005 entitled "Expression Quantification Using Mass Spectrometry;" Inventors; Hunter, et al.; Assignee: Applera Corporation.

USPTO issued Office Action mailed Jun. 12, 2008 in U.S. Appl. No. 11/134,850, filed May 19, 2005 entitled "Expression Quantification Using Mass Spectrometry," Inventors: Hunter, et al.; Assignee: Applera Corporation.

Jenkins, et al., "Relative and absolute quantitative expression profiling of cytochromes P450 using isotope-coded affinity tags", Proteomics, vol. 6, 1934-1947, 2006 (online publication Feb. 14, 2006).

Anderson, et al., "Quantitative Mass Spectrometric Multiple Reaction Monitoring Assays for Major Plasma Proteins", Mol. & Cell Proteomics, vol. 5, pp. 573-588, 2006 (published, MCP Papers in Press Dec. 6, 2005).

EXPRESSION QUANTIFICATION USING MASS SPECTROMETRY

CROSS-REFERENCE TO RELATED APPLICATIONS

The present application is a continuation and claims the right of priority to U.S. application Ser. No. 11/441,457, entitled "Expression Quantification Using Mass Spectrometry", filed May 26, 2006, now abandoned, which is a continuation-in-part of and claims the benefit of and priority to U.S. application Ser. No. 11/134,850, entitled "Expression Quantification Using Mass Spectrometry", filed May 19, 2005, now abandoned, which claims the benefit of and priority to U.S. Provisional Application No. 60/572,826, entitled "Expression Quantification Using Mass Spectrometry", filed May 19, 2004, the entire disclosures of both of which are herein incorporated by reference.

INTRODUCTION

Understanding protein expression is important to understanding biological systems. Unlike mRNA, which only acts as a disposable messenger, proteins implement almost all controlled biological functions and, as a result, are integral to such functions as normal cell activity, disease processes, and drug responses. However, protein expression is not reliably predictable. First, protein expression is not predictable from mRNA expression maps because mRNA transcript levels are not always strongly correlated with protein levels. Second, proteins are dynamically modified in biological systems by environmental factors in ways which are not predictable from genetic information.

Further, the function of a protein can be modulated by its abundance and its degree of modifications. Changes in protein expression (or concentration) and the extent of protein modifications can have a great influence on the activity, for example, of intracellular substrate degradation processes, biosynthetic pathways, the cell cycle, or the function of a single cell in a whole organism. As a result, changes in protein concentration could, for example, provide information on a biological state at the molecular level, on potential drug targets, the toxicity of a drug, the possibility of a drug forming a dangerous metabolite, and serve as biomarkers for certain disease states or markers that predict the likelihood of a positive response to a specialized drug therapy.

In general, approaches to quantifying protein expression fall into two categories, relative quantitation and absolute quantitation. Although absolute quantitation typically provides more information than relative quantitation, it has traditionally been more difficult to implement.

SUMMARY

The present teachings provide systems, methods, assays and kits for the absolute quantitation of protein expression. In various aspects, methods of determining the absolute concentration of one or more isoforms of a protein using standard samples of signature protein fragments and parent-daughter ion transition monitoring (PDITM) are provided. In various embodiments, the protein isoforms comprise one or more isoenzymes, one or more isomers, or combinations thereof. In various embodiments, the absolute concentration of multiple isoforms of a biomolecule in a sample, multiple proteins in a biological process (e.g., to cover families of biomarkers, biological pathways, etc.), a combination of multiple samples, or combinations thereof, can be determined in a multiplex fashion, for example, from a single loading of the sample (or combined samples) onto a chromatographic column followed by PDITM.

The term "parent-daughter ion transition monitoring" or "PDITM" refers to, for example, a measurement using mass spectrometry whereby the transmitted mass-to-charge (m/z) range of a first mass separator (often referred to as the first dimension of mass spectrometry) is selected to transmit a molecular ion (often referred to as "the parent ion" or "the precursor ion") to an ion fragmentor (e.g., a collision cell, photodissociation region, etc.) to produce fragment ions (often referred to as "daughter ions") and the transmitted m/z range of a second mass separator (often referred to as the second dimension of mass spectrometry) is selected to transmit one or more daughter ions to a detector which measures the daughter ion signal. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal". In the present teachings, where the parent ion is a signature peptide and the ion signal of a diagnostic daughter ion is measured, the diagnostic daughter ion signal at the detector for a given signature peptide ion-diagnostic daughter ion combination monitored can be referred to as the "signature peptide-diagnostic daughter ion transition signal".

For example, one embodiment of parent-daughter ion transition monitoring is multiple reaction monitoring (MRM) (also referred to as selective reaction monitoring). In various embodiments of MRM, the monitoring of a given parent-daughter ion transition comprises using as the first mass separator a first quadrupole parked on the parent ion m/z of interest to transmit the parent ion of interest and using as a second mass separator a second quadrupole parked on the daughter ion m/z of interest to transmit daughter ions of interest. In various embodiments, a PDITM can be performed, for example, by parking the first mass separator on parent ion m/z of interest to transmit parent ions and scanning the second mass separator over a m/z range including the m/z value of the daughter ion of interest and, e.g., extracting an ion intensity profile from the spectra.

For example, a tandem mass spectrometer (MS/MS) instrument or, more generally, a multidimensional mass spectrometer ($MS^n$) instrument, can be used to perform PDITM, e.g., MRM.

In various embodiments, one or more proteins of interest can be used for, e.g., normalization of diagnostic daughter ion signals, normalization of the concentration of a protein in a first sample relative the concentration in a second sample (e.g., normalize a concentration ratio), evaluation of data reliability, evaluation of starting sample amount across samples, or combinations thereof. Herein, such proteins are referred to as normalization proteins. Accordingly, in various embodiments, the term "normalization protein" refers to a protein which is anticipated to have substantially the same concentration in two or more of the two or more samples, is anticipated to have a concentration that is not substantially affected by treatment of a sample with a chemical agent, or both. For example, in various embodiments, a protein of interest can be a protein known to have substantially the same concentration between samples. In various embodiments, changes in the signal level of a signature peptide of a normalization protein can be used to normalize the signal levels of the signature peptides of one or more proteins of interest. In various embodiments, differences in the signature peptide signal level of a normalization protein between two samples can be used to evaluate data reliability. For example, where the signature peptide signal associated with a normalization protein varies by a significant amount between samples, the data associated with one or both of these samples is excluded as unreliable. In various embodiments, it is not necessary to determine the absolute concentration of a normalization protein because, e.g., the ratio of the signature peptide signal associated with a normalization protein in one sample to that in another sample can be used to normalize the signal levels of the signature peptides of one or more proteins of interest, the concentration of a protein of interest in one sample relative to that in another sample, evaluation of starting sample amount across samples, evaluate the reliability of data, or combinations thereof.

In various embodiments, provided are methods for determining the concentration of one or more proteins of interest in one or more samples, comprising the steps of: (a) providing a standard sample for each of one or more proteins of interest, each standard sample comprising a signature peptide for the corresponding protein of interest; (b) selecting one or more signature peptide-diagnostic daughter ion transitions for at least one signature peptide of each standard sample; (c) generating a concentration curve for each selected signature peptide-diagnostic daughter ion transition; (d) labeling the one or more proteins of interest in the one or more samples with a chemical moiety; (e) loading at least a portion of each of the one or more labeled samples on a chromatographic column; (f) directing at least a portion of the eluent from the chromatographic column to a mass spectrometry system; (g) measuring the signature peptide-diagnostic daughter ion transition signal of one or more of the selected signature peptide-diagnostic daughter ion transitions; and (h) determining the absolute concentration of a protein of interest in one or more of the labeled samples based at least on a comparison of the measured signature peptide-diagnostic daughter ion transition signal corresponding to the protein of interest to the concentration curve for that signature peptide-diagnostic daughter ion transition. In various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization protein in the second sample; and normalizing the concentration ratio of the protein of interest using the concentration ratio of the normalization protein.

In various embodiments, provided are methods for determining the concentration of one or more proteins of interest in one or more samples, comprising the steps of: (a) providing a standard sample comprising a signature peptide for each corresponding protein of interest; (b) selecting one or more signature peptide-diagnostic daughter ion transitions for each signature peptide; (c) labeling the one or more proteins of interest in the one or more samples with a chemical moiety to produce one or more labeled samples; (d) labeling one or more standard samples with a chemical moiety; (e) combining, to produce a combined sample, at least a portion of the one or more labeled standard samples with at least a portion of one or more labeled samples, the labeled samples being labeled with a different chemical moiety than the one or more labeled standard samples combined therewith; (f) loading at least a portion of each of the one or more combined samples on a chromatographic column; (g) directing at least a portion of the eluent from the chromatographic column to a mass spectrometry system; (h) measuring the signature peptide-diagnostic daughter ion transition signal of one or more of the selected signature peptide-diagnostic daughter ion transitions; and (i) determining the absolute concentration of a protein of interest in one or more of the labeled samples based at least on a comparison of the measured signature peptide-diagnostic daughter ion transition signal for the protein of interest to the measured signature peptide-diagnostic daughter ion transition signal for a labeled standard sample. In various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization protein in the second sample; and normalizing the concentration ratio of the protein of interest using the concentration ratio of the normalization protein.

In various embodiments, provided are methods for determining the concentration of one or more proteins of interest in one or more samples, comprising the steps of: (a) providing a standard sample for each of one or more proteins of interest, each standard sample comprising a signature peptide for the corresponding protein of interest; (b) selecting one or more signature peptide-diagnostic daughter ion transitions for at least one signature peptide of each standard sample; (c) generating a concentration curve for each selected signature peptide-diagnostic daughter ion transition; (d) labeling the one or more proteins of interest in the one or more samples with a chemical moiety; (e) labeling one or more standard samples with a chemical moiety; (f) combining, to produce a combined sample, at least a portion of the one or more labeled standard samples with at least a portion of one or more labeled samples, the labeled sampled being labeled with a different chemical moiety than the one or more labeled standard samples combined therewith; (g) loading at least a portion of each of the one or more combined samples on a chromatographic column; (h) directing at least a portion of the eluent from the chromatographic column to a mass spectrometry system; (i) measuring the signature peptide-diagnostic daughter ion transition signal of one or more of the selected signature peptide-diagnostic daughter ion transitions; and (j) determining the absolute concentration of a protein of interest in one or more of the labeled samples based at least on a comparison of the measured signature peptide-diagnostic daughter ion transition signal corresponding to the protein of interest to one or more of the concentration curve for that signature peptide-diagnostic daughter ion transition and the measured signature peptide-diagnostic daughter ion transition signal for a labeled standard sample. In various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization protein in the second sample; and normalizing the concentration ratio of the protein of interest using the concentration ratio of the normalization protein.

In various embodiments, provided are methods for determining the concentration of one or more proteins of interest in two or more samples, comprising the steps of: (a) providing a standard sample for each of one or more proteins of interest, each standard sample comprising a signature peptide for the corresponding protein of interest; (b) selecting one or more signature peptide-diagnostic daughter ion transitions for at least one signature peptide of each standard sample; (c) generating a concentration curve for each selected diagnostic daughter ion; (d) labeling the one or more proteins of interest in two or more samples with different chemical moieties for each sample, the two or more samples thereby being differentially labeled; (e) combining at least a portion of the differentially labeled samples to produce a combined sample; (f) loading at least a portion of the combined sample on a chromatographic column; (g) directing at least a portion of the eluent from the chromatographic column to a mass spectrometry system; (h) measuring the signature peptide-diagnostic daughter ion transition signal of one or more of the selected signature peptide-diagnostic daughter ion transitions; and (i) determining the absolute concentration of a protein of interest in one or more of the differentially labeled samples based at least on a comparison of the measured signature peptide-diagnostic daughter ion transition signal for the protein of interest to the concentration curve for that signature peptide-diagnostic daughter ion transition. In various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization protein in the second sample; and normalizing the concentration ratio of the protein of interest using the concentration ratio of the normalization protein.

In various embodiments, provided are methods for determining the concentration of one or more proteins of interest in two or more samples, comprising the steps of: (a) providing a standard sample for each of one or more proteins of interest, each standard sample comprising a signature peptide for the corresponding protein of interest; (b) selecting one or more signature peptide-diagnostic daughter ion transitions for at least one signature peptide of each standard sample; (c) labeling the one or more proteins of interest in two or more samples with different chemical moieties for each sample, the two or more samples thereby being differentially labeled; (d) labeling one or more standard samples with a chemical moiety; (e) combining, to produce a combined sample, at least a portion of the one or more labeled standard samples with at least a portion of two or more differentially labeled samples, the differentially labeled samples being labeled with a different chemical moiety than the one or more labeled standard samples combined therewith; (f) loading at least a portion of the combined sample on a chromatographic column; (g) directing at least a portion of the eluent from the chromatographic column to a mass spectrometry system; (h) measuring the signature peptide-diagnostic daughter ion transition signal of one or more of the selected signature peptide-diagnostic daughter ion transitions; and (i) determining the absolute concentration of a protein of interest in one or more of the differentially labeled samples based at least on a comparison of the measured signature peptide-diagnostic daughter ion transition signal for the protein of interest to the measured signature peptide-diagnostic daughter ion transition signal for a labeled standard sample. In various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization protein in the second sample; and normalizing the concentration ratio of the protein of interest using the concentration ratio of the normalization protein.

In various embodiments, provided are methods for determining the concentration of one or more proteins of interest in two or more samples, comprising the steps of: (a) providing a standard sample for each of one or more proteins of interest, each standard sample comprising a signature peptide for the corresponding protein of interest; (b) selecting one or more signature peptide-diagnostic daughter ion transitions for at least one signature peptide of each standard sample; (c) generating a concentration curve for each selected diagnostic daughter ion; (d) labeling the one or more proteins of interest in two or more samples with different chemical moieties for each sample, the two or more samples thereby being differentially labeled; (e) labeling one or more standard samples with a chemical moiety; (f) combining, to produce a combined sample, at least a portion of the one or more labeled standard samples with at least a portion of two or more differentially labeled samples, the differentially labeled samples being labeled with a different chemical moiety than the one or more labeled standard samples combined therewith; (g) loading at least a portion of the combined sample on a chromatographic column; (h) directing at least a portion of the eluent from the chromatographic column to a mass spectrometry system; (i) measuring the signature peptide-diagnostic daughter ion transition signal of one or more of the selected signature peptide-diagnostic daughter ion transitions; and (j) determining the absolute concentration of a protein of interest in one or more of the labeled samples based at least on a comparison of the measured signature peptide-diagnostic daughter ion transition signal corresponding to the protein of interest to one or more of the concentration curve for that signature peptide-diagnostic daughter ion transition and the measured signature peptide-diagnostic daughter ion transition signal for a labeled standard sample. In various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization protein in the second sample; and normalizing the concentration ratio of the protein of interest using the concentration ratio of the normalization protein.

The standard samples comprising a signature peptide for the corresponding protein of interest (also referred to herein as "signature peptide standard samples") are used, in various embodiments, to generate a concentration curve for each signature peptide and, in various embodiments, can act as an internal standard when measuring unknown samples. In various embodiments, the standard peptides can act as concentration normalizing standards when measuring unknown samples. In various embodiments, a standard sample comprises a signature peptide for a normalization protein.

In the present teachings a standard sample can be provided in a variety of ways. In various embodiments, a standard sample can be provided as a synthetic peptide, which is labeled and added in a known concentration to a sample under investigation to provide an internal standard. In various embodiments, a standard sample is provided from a control sample containing one or more proteins of interest. The control sample can be subjected to fragmentation (e.g., digestion) prior to or after labeling with a tag. The tag thus can be used to label one or more signature peptides in the one or more proteins of interest. The labeled control sample can be added to a sample under investigation to provide an internal standard. In various embodiments, the labeled control sample is added in a known concentration and can be used to determine absolute concentrations of one or more proteins of interest in the sample under investigation. In various embodiments, the labeled control sample is added at a fixed amount to a set of samples and can be used to determine the relative concentrations of one or more proteins of interest between the sets of samples under investigation.

A control sample can be provided in a variety of ways. For example, a control sample can comprise, for example, a normal sample, a pooled reference standard from all or some of the samples to be analyzed, or combinations thereof. For example, in various embodiments, a control sample comprises a normal patient sample that can serve as an internal standard to determine if samples under investigation differ from the normal sample, and thus, e.g., providing a potential indication of a disease state for a disease state. In various embodiments, the control sample is mixed into every sample to be analyzed at a substantially fixed ratio. In various embodiments, a fixed ratio of about 1:1 is used and, for example, can facilitate observation of both up-regulated and down-regulated peptides, proteins or both.

In various embodiments, the proteins of interest comprise cytochrome P450 isoforms, which include, but are not limited to, one or more of Cyp1a1, Cyp1a2, Cyp1b1, Cyp2a4, Cyp2a12, Cyp2b6, Cyp2b10, Cyp2c8, Cyp2c9, Cyp2c19, Cyp2c29/Cyp2c37, Cyp2c39, Cyp2c40, Cyp2d6, Cyp2d9, Cyp2d22/Cyp2d26, Cyp2e1, Cyp2f2, Cyp2j5, Cyp3a4, Cyp3a11, Cyp4a10/Cyp4a14, and combinations thereof. In various embodiments, the signature peptides comprise one or more of: CIGETIGR (SEQ. ID NO. 1), CIGEIPAK (SEQ. ID NO. 2); CIGEELSK (SEQ. ID NO. 3); YCFGEGLAR (SEQ. ID NO. 4); FCLGESLAK (SEQ. ID NO. 5); 1CLGESIAR (SEQ. ID NO. 6); ICAGEGLAR (SEQ. ID NO. 7); VCAGEGLAR (SEQ. ID NO. 8); ICVGESLAR (SEQ. ID NO. 9); SCLGEALAR (SEQ. ID NO. 10); SCLGEPLAR (SEQ. ID NO. 11); VCVGEGLAR (SEQ. ID NO. 12); LCLGEPLAR (SEQ. ID NO. 13; ACLGEQLAK (SEQ. ID NO. 14); NCLGMR (SEQ. ID NO. 15); and NCIGK (SEQ. ID NO. 16); YIDLLPTSLPHAVTCDIK (SEQ. ID NO. 17); ICVGEGLAR (SEQ. ID NO. 18); ACLGEPLAR(SEQ. ID NO. 19); CIGEVLAK (SEQ. ID NO. 20); GFCMFDMECHK (SEQ. ID NO. 21); ICLGEGIAR (SEQ. ID NO. 22); LCQNEGCK (SEQ. ID NO. 23); GCPSLSELWR (SEQ. ID NO. 24); EECALEIIK (SEQ. ID NO. 25); GCPSLAEHWK (SEQ. ID NO. 26); VFANPEDCAFGK (SEQ. ID NO. 27).

In various embodiments, the present teachings facilitate identifying therapeutic candidate compounds, including antibodies and cellular immunotherapies. In various embodiments, the present teachings facilitate the study of drug metabolizing enzymes, (for example, cytochromes P450, uridine 5'-triphosophate glucuronosyltransferases, etc.). For example, the cytochrome P450 protein family of mono-oxygenases is responsible for the regulation of drug elimination in the liver and the formation of toxic drug metabolites. There are four major families of P450 isoforms with about 25 different isoforms, each with different substrate specificities inducible by different drugs or chemicals. This enzymatic behavior can make this family of proteins important in drug development. For example, the changes in expression of the different P450 proteins can provide information on the toxicity of different drugs and the possibility of forming dangerous drug metabolites. A system, method or assay to screen for multiple P450 isoforms could be of value in drug development, particularly if it yielded quantitative data relating to expression changes for individual isoforms.

In various aspects, provided are methods of assessing the response of a biological system to a chemical agent, comprising the steps of: (a) determining the absolute concentration of two or more proteins in a biological sample not exposed to a chemical agent; (b) determining the absolute concentration of two or more proteins in a biological sample exposed to the chemical agent; and (c) assessing the response of a biological system to the chemical agent based at least on the comparison of one or more of the absolute concentrations determined in step (a) to one or more of the absolute concentrations determined in step (b). In various embodiments, examples of biological systems (e.g., in vivo, in vitro, in silico, or combinations thereof) include, but are not limited to, whole organisms (e.g., a mammal, bacteria, virus, etc.), one or more sub-units of an whole organism (e.g., organ, tissue, cell, etc.), a biological or biochemical process, a disease state, a cell line, models thereof, and combinations thereof. In various embodiments, the chemical agent comprises one or more pharmaceutical agents, pharmaceutical compositions, or combinations thereof.

In various embodiments, the determination of absolute concentrations in the methods of assessing the response of a biological system to a chemical agent comprises one or more of the methods for determining the concentration of one or more proteins of interest in one or more samples described herein, one or more of the methods for determining the concentration of one or more proteins of interest in two or more samples described herein, or combinations thereof.

In various aspects, provided are assays designed to determine the level of expression of two or more proteins of interest in one or more samples. The assay can be, for example, an endpoint assay, a kinetic assay, or a combination thereof. The assay can, for example, be diagnostic of a disease or condition, prognostic of a disease or condition, or both. In various embodiments, provided are assays for determining the level of expression of two or more proteins in one or more samples using a method of the present teachings, comprises one or more of the methods for determining the concentration of one or more proteins of interest in one or more samples described herein, one or more of the methods for determining the concentration of one or more proteins of interest in two or more samples described herein, or combinations thereof.

In various aspects, provided are kits for performing a method, assay, or both of the present teachings. In various embodiments, a kit comprises two or more signature peptide standard samples, the signature peptides of two or more of the two or more signature peptide standard samples being signature peptides of different proteins. In various embodiments, a kit comprises five or more signature peptide standard samples, the signature peptides of ten or more of the five or more signature peptide standard samples being signature peptides of different cytochrome P450 isoforms. In various embodiments, a kit comprises ten or more signature peptide standard samples, the signature peptides of ten or more of the ten or more signature peptide standard samples being signature peptides of different cytochrome P450 isoforms.

In various embodiments, a kit comprises one or more signature peptide standard samples for one or more normalization proteins. For example, in various embodiments, a kit comprises one or more labeled signature peptide standard samples for normalization proteins where the signature peptides comprise one or more of: LCQNEGCK (SEQ. ID NO. 23); EECALEIIK (SEQ. ID NO. 25); GCPSLAEHWK (SEQ. ID NO. 26); and VFANPEDCAFGK (SEQ. ID NO. 27).

In various embodiments, a kit comprises signature peptide standard samples for signature peptides of one or more of the normalization proteins: corticosteroid 11-beta dehydrogenase isozyme 1, triglyceride transfer protein, and microsomal glutathione S-transferase.

In various embodiments, a kit for performing a method, assay, or both of the present teachings, on one or more samples derived from a mouse comprises signature peptide standard samples for signature peptides of one or more of the normalization proteins: corticosteroid 11-beta dehydrogenase isozyme 1, triglyceride transfer protein, microsomal glutathione S-transferase.

In various embodiments, a sample is derived from microsomal cells. Examples of suitable normalization proteins for microsomal cell derived samples include, but are not limited to: corticosteroid 11-beta dehydrogenase isozyme 1, triglyceride transfer protein, microsomal glutathione S-transferase, where, in various embodiments, the signature peptides are, respectively, LCQNEGCK (SEQ. ID NO. 23); EECALEIIK (SEQ. ID NO. 25); GCPSLAEHWK (SEQ. ID NO. 26); VFANPEDCAFGK (SEQ. ID NO. 27) (e.g., for mouse) or LCQNEGCK (SEQ. ID NO. 23); GCPSLSELWR (SEQ. ID NO. 24); EECALEIIK (SEQ. ID NO. 25); (e.g., for human) LCQNEGCK (SEQ. ID NO. 23); EECALEIIK (SEQ. ID NO. 25) (e.g., for mouse and human).

In various embodiments, a kit comprises signature peptide standard samples for signature peptides of the cytochrome P450 isoforms Cyp2a4, Cyp2a12, Cyp2b10, Cyp2c29/Cyp2c37, and Cyp2c40. In various embodiments, a kit comprises labeled signature peptide samples wherein the signature peptides comprise: YCFGEGLAR (SEQ. ID NO. 4); FCLGESLAK (SEQ. ID NO. 5); ICLGESIAR (SEQ. ID NO. 6); ICAGEGLAR (SEQ. ID NO. 7); and ICVGESLAR (SEQ. ID NO. 9). In various embodiments, a kit comprises signature peptide standard samples for signature peptides of one or more of the cytochrome P450 isoforms Cyp1a1, Cyp1a2, Cyp1b1, Cyp2a4, Cyp2a12, Cyp2b6, Cyp2b10, Cyp2c8, Cyp2c9, Cyp2c19, Cyp2c29/Cyp2c37, Cyp2c39, Cyp2c40, Cyp2d6, Cyp2d9, Cyp2d22/Cyp2d26, Cyp2e1, Cyp2f2, Cyp2j5, Cyp3a4, Cyp3a11, Cyp4a10/Cyp4a14, and combinations thereof. In various embodiments, the signature peptides comprise one or more of: CIGETIGR (SEQ. ID NO. 1), CIGEIPAK (SEQ. ID NO. 2); CIGEELSK (SEQ. ID NO. 3); YCFGEGLAR (SEQ. ID NO. 4); FCLGESLAK (SEQ. ID NO. 5); ICLGESIAR (SEQ. ID NO. 6); ICAGEGLAR (SEQ. ID NO. 7); VCAGEGLAR (SEQ. ID NO. 8); ICVGESLAR (SEQ. ID NO. 9); SCLGEALAR (SEQ. ID NO. 10); SCLGEPLAR (SEQ. ID NO. 11); VCVGEGLAR (SEQ. ID NO. 12); LCLGEPLAR (SEQ. ID NO. 13; ACLGEQLAK (SEQ. ID NO. 14); NCLGMR (SEQ. ID NO. 15); and NCIGK (SEQ. ID NO. 16); YIDLLPTSLPHAVTCDIK (SEQ. ID NO. 17); ICVGEGLAR(SEQ. ID NO. 18); ACLGEPLAR(SEQ. ID NO. 19); CIGEVLAK (SEQ. ID NO. 20); GFCMFDMECHK (SEQ. ID NO. 21); ICLGEGIAR (SEQ. ID NO. 22); LCQNEGCK (SEQ. ID NO. 23); GCPSLSELWR (SEQ. ID NO. 24); EECALEIIK (SEQ. ID NO. 25); GCPSLAEHWK (SEQ. ID NO. 26); VFANPEDCAFGK (SEQ. ID NO. 27) and combinations thereof.

As will be appreciated more fully from the following description in conjunction with the drawings, various embodiments of the present teachings can provide methods that facilitate the discovery, verification and/or validation of biomarkers; that facilitate the elucidation of basic biology and cell signaling; that facilitate drug discovery, or combinations thereof.

In various embodiments the present teachings can elucidation of basic biology and cell signaling, for example, by facilitating the ability to quantitatively measure amount of a protein or proteins involved in a pathway; e.g., a labeled control standard being created from a "resting state" sample and being added into labeled perturbed state samples to facilitate quantitatively measuring changes in protein expression between resting and perturbed states.

In various embodiments the present teachings can facilitate drug discovery, for example, by facilitating the determination of the biological pathways effected by an agent. For example, various embodiments of the present teachings can be used to investigate a panel of proteins that represent good, or potential, drug targets. The method could be used to analyze samples that have been treated with a drug candidate to determine if any pathways have been affected, e.g., advantageous, negatively (e.g., toxic effect), or both. In various embodiments, a panel of proteins can be chosen to cover a broad spectrum of cellular pathways; and, for example, the qualitative and/or quantitative changes in protein expression used to obtain a greater understanding of the mode of action of the candidate therapeutic, the actual target, etc.

The foregoing and other aspects, embodiments, and features of the teachings can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the teachings.

DETAILED DESCRIPTION OF VARIOUS EMBODIMENTS

Figure 1A:
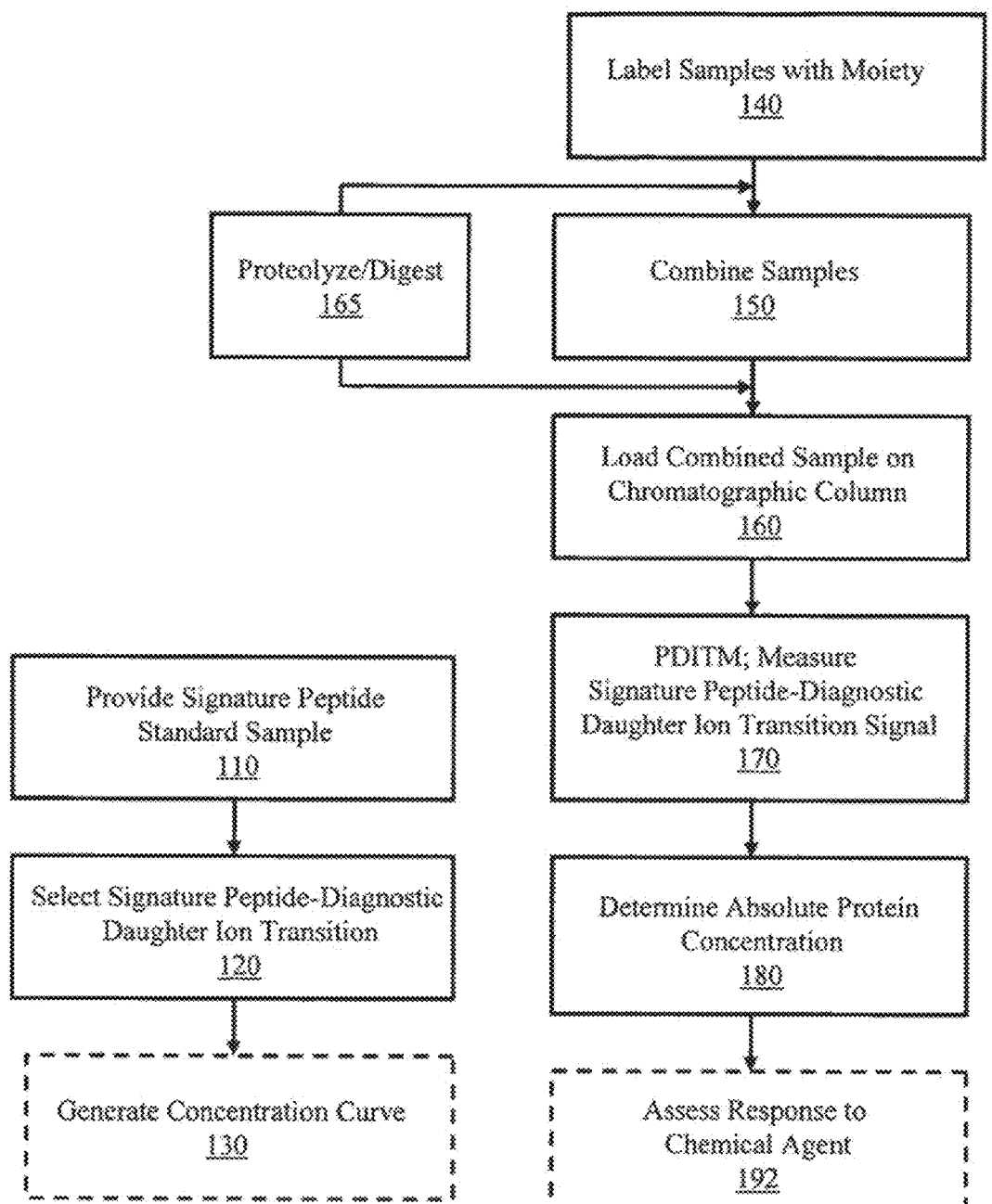
FIGS. 1A and 1B are a schematic diagram of various embodiments of methods of determining the absolute concentration of a protein in a sample.
Figure 1B:

Referring to FIGS. 1A and 1B, in various embodiments, methods for determining the absolute concentration of a protein in a sample provide a signature peptide standard sample (step 110) for each protein of interest in one or more samples. For example, for each individual protein isoform of interest, a peptide substantially unique to the individual isoform is selected as a signature peptide for that isoform. In various embodiments, more than one signature peptide can be selected for a given isoform and a signature peptide standard sample can be prepared for each of the selected signature peptides of that isoform (e.g., the use of multiple signature peptides for a single protein can provide cross-verification of the concentrations determined using the different signature peptide standard samples for that protein). The signature peptide standard samples can be derived, for example, from proteins that are known and/or anticipated to be unchanged by the conditions of the experiment. For example, the signature peptide standard can be derived from a control sample containing one or more of the proteins of interest, such as, e.g., a normal patient sample, a known concentration sample, etc. The signature peptide standard samples can be unlabeled or labeled with a chemical moiety.

A sample of the signature peptide for each isoform of interest can be prepared synthetically and labeled with a chemical moiety. A sample of the signature peptide for each isoform can be prepared by labeling with a chemical moiety non-synthetic isoforms in one or more samples prior to or after digestion of the isoforms in the one or more samples. Examples of chemical moieties suitable for labeling include, but are not limited to, labeling with an isotope coded affinity tag (e.g., an ICAT® brand reagent), with an isobaric (same mass) tag (e.g. ITRAQT™ reagent), a mass differential tag (e.g., a MTRAQ™ brand reagent) etc.; and the concentration of the signature peptide in each labeled signature peptide sample can be determined using, for example, amino acid analysis (AAA) on a portion of the sample.

In various embodiments, the signature peptide standard sample is cleaned up (e.g., to remove, e.g., interfering sample, buffer artifacts, etc; by, e.g., high performance liquid chromatography (HPLC), reverse phase (RP)-HPLC, exchange fractionation, etc., and combinations thereof) before the concentration of the signature peptide in the labeled signature peptide sample is determined. In various embodiments, the signature peptide standard sample is labeled with substantially the same chemical moiety as applied to one or more of the samples to be analyzed. In various embodiments, the signature peptide standard sample is labeled with a different chemical moiety as applied to one or more of the samples (such as, e.g., when a signature peptide standard sample is used an internal standard). For example, in various embodiments, a standard sample comprises a signature peptide for a normalization protein.

At least a portion of a signature peptide standard sample can be subjected to PDITM scans (e.g. MRM scans) to select one or more diagnostic daughter ions for that signature peptide (step 120) and thereby select a signature peptide-daughter ion transition for the signature peptide of the standard sample. It is to be understood that same diagnostic daughter ion (e.g., having the same mass, the same structure, etc.) can be selected for different signature peptides. In various embodiments, the signature peptide standard sample is cleaned up (e.g., to remove, e.g., interfering sample, buffer artifacts, etc; by, e.g., high performance liquid chromatography (HPLC), reverse phase (RP)-HPLC, exchange fractionation, etc., and combinations thereof) before it is used to select a diagnostic daughter ion. Diagnostic daughter ions for a signature peptide can be selected, for example, based on one or more of their: level of detection (LOD), limit of quantitation (LOQ), signal-to-noise (S/N) ratio, mass similarity with other daughter ions of other signature peptides, and linearity of quantitation over a specific dynamic range of concentrations. In various embodiments, the dynamic range of concentrations of interest is about three to about four orders of magnitude depending, for example, on the mass analyzer system being used. In various embodiments, the LOQ ranges from about attomole levels ($10^{-18}$ moles) to about femtomole levels ($10^{-15}$ moles) per microgram (μg) of sample, with a dynamic range of about three to about four orders of magnitude above the LOQ.

The same signature peptide standard sample portion used to select a diagnostic daughter ion or another portion of a signature peptide standard sample can be used to determine parent-daughter ion transition monitoring conditions for the mass analyzer system. For example, where the mass analyzer system comprises a liquid chromatography (LC) component, the signature peptide standard sample can be used to determine chromatography retention times. In various embodiments, the signature peptide standard sample can be used to determine for the signature peptide in the sample its ionization efficiency in the ion source and fragmentation efficiency in the ion fragmentor under various conditions.

Referring again to FIGS. 1A and 1B, in various embodiments, the same portion used to select a diagnostic daughter ion or another portion of a signature peptide standard sample is subject to PDITM to generate one or more concentrations curves for the selected signature peptide-diagnostic daughter ion transition (step 130) based on the ion signal for the corresponding diagnostic daughter ion. The ion signal for the diagnostic daughter ion can, for example, be based on the intensity (average, mean, maximum, etc.) of the diagnostic daughter ion peak, the area of the diagnostic daughter ion peak, or a combination thereof. In various embodiments, the generation of a concentration curve can use one or more internal standards included in at least a portion of the signature peptide standard sample to, e.g., facilitate concentration determinations, account for differences in injection volume, etc.

In various embodiments, a concentration curve can be generated by using PDITM to measure the ion signal of a diagnostic daughter ion associated with the corresponding signature peptide standard sample; and generating a concentration curve by linear extrapolation of the measured concentration such that zero concentration corresponds to zero diagnostic daughter ion signal. In various embodiments, a concentration curve can be generated by using PDITM to measure the ion signal of a diagnostic daughter ion associated with the corresponding signature peptide standard sample at two or more known concentrations; and generating a concentration curve by fitting a function to the measured diagnostic daughter ion signals. Suitable fitting functions can depend, for example, on the response of the detector (e.g., detector saturation, non-linearity, etc.). In various embodiments, the fitting function is a linear function.

In various embodiments, sample preparation and signature peptide standard sample preparation label proteins, peptides, or both, with a chemical moiety (e.g., tag). A wide variety of chemical moieties and labeling approaches can be used in the present teachings. For example, differentially isotopically labeled protein reactive reagents, as described in published PCT patent application WO 00/11208, the entire contents of which are incorporated herein by reference, can be used to label one or more signature peptides with a chemical moiety. In various embodiments, mass differential reagents, such as, for example, the MTRAQ™ brand reagent method can be used. In various embodiments, labeling of proteins with isotopically coded affinity reagents such as, for example, the ICAT® brand reagent method can be used. In various embodiments, isobaric reagents (reagents which provide labels which are of the same mass but which produce different signals following labeled parent ion fragmentation, e.g., by collision induced dissociation (CID) such as, for example, the ITRAQ™ brand reagent method) can be used. In various embodiments, a set of isobaric (same mass) reagents which yield amine-derivatized peptides that are chromatographically identical and indistinguishable in MS, but which produce strong low-mass MS/MS signature ions following CID can be used. In various embodiments, an affinity separation can be performed on one or more proteins, peptides, or both, of one or more samples before, after, or both before and after, labeling with one or more isobaric reagents.

In various embodiments, the isotope coded affinity labeled protein reactive reagents have three portions: an affinity label (A) covalently linked to a protein reactive group (PRG) through a cleavable linker group (L) that includes an isotopically labeled linker. The tinker can be directly bonded to the protein reactive group (PRG). The affinity labeled protein reactive reagents can have the formula:

The linker can be differentially isotopically labeled, e.g., by substitution of one or more atoms in the linker with a stable isotope thereof. For example, hydrogens can be substituted with deuteriums ($^2H$) and/or $^{12}C$ substituted with $^{13}C$. Utilization of $^{13}C$ promotes co-elution of the heavy and light isotopes in reversed phase chromatography.

The affinity label (A) can function as a means for separating reacted protein (labeled with a PRG) from unreacted protein (not labeled with a PRO) in a sample. In various embodiments, the affinity label comprises biotin. After reaction of the PRG portion of the reagent with protein, affinity chromatography can be used to separate labeled and unlabeled components of the sample. Affinity chromatography can be used to separate labeled and unlabeled proteins, labeled and unlabeled digestion products of the proteins (i.e., peptides) or both. Thereafter, the cleavage of the cleavable linker (L) can be effected such as, for example, chemically, enzymatically, thermally or photochemically to release the isolated materials for mass spectrometric analysis. In various embodiments, the linker can be acid-cleavable.

In various embodiments the PRG can be incorporated on a solid support (S) as shown in the following formula:

The solid support can be composed of, for example, polystyrene or glass, to which cleavable linker and protein reactive groups are attached. The solid support can be used as a means of peptide separation and sample enrichment (e.g., as chromatography media in the form of a column). Unlabeled digestion products, for example, can be linked to the modified solid support via the PRG, labeled and then released by various means (e.g. chemical or enzymatic) from the solid support.

Prior to mass spectrometric analysis, the bound protein can be digested to form peptides including bound peptides which can be analyzed by mass spectrometry. The protein digestion step can precede or follow cleavage of the cleavable linker. In some embodiments, a digestion step (e.g., enzymatic cleavage) may not be necessary, where, for example, the proteins are relatively small. In various embodiments, the insertion of an acid cleavable linker can result in a smaller and more stable label. A smaller and more stable linker can afford enhanced ion fragmentation, e.g., in CID.

Examples of PRG groups include, but are not limited to: (a) those groups that selectively react with a protein functional group to form a covalent or non-covalent bond tagging the protein at specific sites, and (b) those that are transformed by action of the protein, e.g., that are substrates for an enzyme. In various embodiments, a PRG can be a group having specific reactivity for certain protein groups, such as specificity for sulfhydryl groups. Such a PRG can be useful, for example, in general for selectively tagging proteins in complex mixtures. For example, a sulfhydryl specific reagent tags proteins containing cysteine.

In various embodiments, a PRG group that selectively reacts with certain groups that are typically found in peptides (e.g., sulfhydryl, amino, carboxy, hydroxy, lactone groups) can be introduced into a mixture containing proteins. In various embodiments, after reaction with the PRG, proteins in the complex mixture are cleaved, e.g., enzymatically, into a number of peptides.

Referring again to FIGS. 1A and 1B, the determination of the absolute concentration of one or more proteins in one or more samples proceeds with labeling one or more of the proteins in one or more of the samples (step 140) with a chemical moiety. In various embodiments, this step of labeling comprises differentially labeling one or more proteins in two or more samples, where different chemical moieties are used to label proteins in different samples. A wide variety of chemical moieties can be used to perform the labeling, differential labeling, or both, including, but not limited to, those described above and elsewhere herein. For example, isotopically different labels, different isobaric reagents, or combinations thereof can be used to differentially label samples. A wide variety of samples can be used including, but not limited to, biological fluids, and cell or tissue lysates. The samples can be from different sources or conditions, for example, control vs. experimental, samples from different points in time (e.g., to form a sequence), disease vs. normal, experimental vs. disease, etc.

In various embodiments, differential labeling is used for multiplexing, so that within one experimental run, for example, multiple different isoforms from different samples (e.g., control, treated) can be compared; multiple mutant strains can be compared with a wild type; in a time course scenario, multiple dosage levels can be assessed against a baseline; different isolates of cancer tissue can be evaluated against normal tissue; or combinations thereof in a single run.

In various embodiments, differential labeling on subclasses of peptides (e.g. phosphorylation), can be used to uncover post-translational modifications (PTM's).

In various embodiments, at least a portion of the labeled samples, labeled signature peptide standard samples, or both, are then combined (step 150) and at least a portion of the combined sample is loaded on a chromatographic column (step 160) (e.g., a LC column, a gas chromatography (GC) column, or combinations thereof). In various embodiments, labeled samples, labeled signature peptide standard samples, or both, are combined (step 150) according to one or more of the following to produce a combined sample:

(i) a labeled sample (e.g., a control sample, an experimental sample) is combined with one or more signature peptide standard samples (the signature peptides of the standard samples corresponding to the signature peptides of one or more proteins of interest);

(ii) a labeled sample (e.g., a control sample, an experimental sample) is combined with one or more labeled signature peptide standard samples, the signature peptides of the standard samples corresponding to the signature peptides of one or more proteins of interest and the labeled signature peptide samples being differentially labeled with respect to the labeled sample;

(iii) two or more differentially labeled samples (e.g., control and experimental; experimental #1 and experimental #2; multiple controls and multiple experimental samples; etc) are combined;

(iv) two or more differentially labeled samples are combined with one or more signature peptide standard samples;

(v) two or more differentially labeled samples are combined with one or more labeled signature peptide standard samples, the labeled signature peptide standard samples being differentially labeled with respect to the differentially labeled samples; and/or (vi) combinations thereof.

For example, the addition of a signature peptide standard sample can serve as an internal standard for the corresponding signature peptide. In various embodiments, a signature peptide standard sample comprises a signature peptide for a normalization protein. A signature peptide standard sample combined with a sample can be referred to as a "signature peptide internal standard sample". Accordingly, in various embodiments, a signature peptide standard sample for each protein of interest in a sample is combined with the sample prior to loading on the chromatographic column. In various embodiments, the different samples are combined in substantially equal amounts.

For example, in various embodiments, a control standard can be provided that is labeled with one reagent from a label from a set of labeling reagents (e.g., ICAT® brand reagents, ITRAQ™ brand reagents, MTRAQ™ brand reagents, etc.) to produce a labeled signature peptide standard sample. It is to be understood that the labeled signature peptides of this standard may still be part of a larger protein until subjected to, for example, digestion. This labeled control standard can be added into each of the labeled samples to be analyzed to produce a combined sample, and. The labeled samples being labeled with a different label than the label used in producing the labeled control standard.

A protein digestion step (step 165) can precede, follow, or both proceed and follow the step of combining (step 150). In various embodiments, proteins in a sample, the combined sample, or both are enzymatically digested (proteolyzed), to generate peptides (step 165). In some embodiments, a digestion step (e.g., enzymatic cleavage) may not be necessary, where, for example, the proteins are relatively small.

At least a portion of the eluent from the chromatographic column is then directed to a mass spectrometry system and the signature peptide-diagnostic daughter ion transition signal of one or more selected signature peptide—diagnostic daughter ion transitions is measured (step 170) using PDITM (e.g., MRM). The mass analyzer system comprises a first mass separator, and ion fragmentor and a second mass separator. The transmitted parent ion ink range of a PDITM scan (selected by the first mass separator) is selected to include a m/z value of one or more of the signature peptides and the transmitted daughter ion m/z range of a PDITM scan (selected by the second mass separator) is selected to include a m/z value one or more of the selected diagnostic daughter ions corresponding to the transmitted signature peptide.

The absolute concentration of a protein of interest in a sample is then determined (step 180). In various embodiments, the absolute concentration of a protein of interest is determined by comparing the measured ion signal of the corresponding signature peptide-diagnostic daughter ion transition (the signature peptide-diagnostic daughter ion transition signal) to one or more of:

(i) the concentration curve for that signature peptide-diagnostic daughter ion transition;

(ii) the signature peptide-diagnostic daughter ion transition signal for a signature peptide internal standard sample;

(iii) the concentration curve for that signature peptide-diagnostic daughter ion transition and the signature peptide-diagnostic daughter ion transition signal for a signature peptide internal standard sample; and/or (iv) combinations thereof.

In various embodiments, one or more proteins of interest can be used for, e.g., normalization of diagnostic daughter ion signals, normalization of the concentration of a protein in a first sample relative the concentration in a second sample (e.g., normalize a concentration ratio), evaluation of data reliability, evaluation of starting sample amount across samples, or combinations thereof. Accordingly, in various embodiments, one or more proteins of interest are normalization proteins which, e.g., are anticipated to have substantially the same concentration in two or more of the two or more samples, are anticipated to have a concentration that is not substantially affected by treatment of a sample with a chemical agent, or both. For example, in various embodiments, a protein of interest can be a protein known to have substantially the same concentration between samples.

In various embodiments, changes in the signal level of a signature peptide of a normalization protein can be used to normalize the signal levels of the signature peptides of one or more proteins of interest. In various embodiments, the relative signal level of a signature peptide of a normalization protein between two samples is used to normalize the relative concentration of a protein of interest between two samples. For example, in various embodiments, the methods comprise a step of assessing the response of a biological system to a chemical agent, assessing the disease state of a biological system, or both, based at least on a comparison of the absolute concentrations of two or more proteins in one or more of the two or more samples. In various embodiments, the step of assessing comprises determining a concentration ratio between two samples for a protein of interest by comparing the concentration of a protein of interest in a first sample relative to the concentration of said protein of interest in a second sample, determining a concentration ratio between two samples for a normalization protein by comparing the concentration of normalization protein in the first sample relative to the concentration of said normalization in the second sample; and normalizing the concentration ratio of the protein of interest using the concentration ratio of the normalization protein. For example, in various embodiments where the ratio of the normalization signature peptide signal between two samples (e.g., control vs. experimental, samples from different points in time (e.g., to form a sequence), disease vs. normal, experimental vs. disease, etc.) varies from 1:1, such a variation can be indicative of, e.g., differences in starting amounts between the two sample, sample handling error, or other systematic or random errors. In various embodiments, the ratio of the normalization signature peptide signal between two samples is used to normalize the concentration ratio of a protein of interest for these two samples. In various embodiments, the ratio for the normalization protein is used as a median ratio and the concentration ratios of one or more proteins of interest are corrected to this median.

In various embodiments, differences in the signature peptide signal level of a normalization protein between two samples can be used to evaluate data reliability. For example, where the signature peptide signal associated with a normalization protein varies by a significant amount between samples, the data associated with one or both of these samples is excluded as unreliable. In various embodiments, variations by more than about one standard deviation are considered significant. In various embodiments, variations by more than about two standard deviations are considered significant. In various embodiments, where the ratio of the normalization signature peptide signal between two samples differs significantly from 1:1 the data associated with one or both of these samples is considered unreliable. In various embodiments, where the diagnostic daughter ion signal of the normalization protein in one sample varies by more than about ±10% relative to the diagnostic daughter ion signal in another sample, such variation is considered significant. In various embodiments, where the diagnostic daughter ion signal of the normalization protein in one sample varies by more than about ±20% relative to the diagnostic daughter ion signal in another sample, such variation is considered significant. In various embodiments, where the diagnostic daughter ion signal of the normalization protein in one sample varies by more than about ±50% relative to the diagnostic daughter ion signal in another sample, such variation is considered significant.

In various embodiments, the standard sample comprises a labeled pooled reference standard. A pooled reference sample can be created in a variety of ways, for example, a pooled reference sample can be provided from a number of patient samples sharing a common feature (all substantially lacking a certain disease state, all possessing a certain disease state, all under a certain age, etc.); a portion of one or more of the samples under investigation, and combinations thereof. Accordingly, in various embodiments, a pooled reference sample is substantially similar in its components to the sample of interests. For example, where a pooled reference sample is provided by combining a portion of each of the samples under investigation, In every peptide in the labeled samples of interest has a corresponding labeled peptide in the labeled standard sample.

In various embodiments, the measured ion signal for the selected diagnostic daughter ion corresponding to the protein of interest from a labeled pooled reference sample can be used to compare relative changes in peptide/protein concentration across many samples which have had the same pooled reference standard added in at equivalent ratios. Accordingly, in various embodiments, a pooled reference sample can be used as a normalization sample. It is to be understood, this comparison might not reflect the absolute amount of protein present but can be used to determine the relative differences between the samples of that protein analyzed on different instruments, under different conditions, etc.

Generally in the present teachings, it is not necessary to determine the absolute concentration of a normalization protein because, e.g., the ratio of the signature peptide signal associated with a normalization protein in one sample to that in another sample can be used to normalize the signal levels of the signature peptides of one or more proteins of interest, normalization of diagnostic daughter ion signals, normalization of the concentration of a protein in a first sample relative the concentration in a second sample (e.g., normalize a concentration ratio), evaluate the reliability of data, evaluation of starting sample amount across samples, or combinations thereof.

In various embodiments, the absolute concentration determinations can be used to understand the basal expression levels of proteins of interest in wild-type or control sample or populations of samples. In various embodiments, the absolute concentration determinations can be applied to screen for and identify proteins which exhibit differential expression in cells, tissue or biological fluids. In various embodiments, the absolute concentration determinations can be used to assess the response of a biological system to a chemical agent (step 192). For example, the absolute concentrations can be used to determine the response of a patient, or a model (e.g., animal, disease, cell, biochemical, etc.) to treatment by a pharmaceutical agent or pharmaceutical composition, exposure to an organism (e.g., virus, bacteria), an environmental contaminant (e.g., toxin, pollutant), etc.

A wide variety of mass analyzer systems can be used in the present teachings to perform PDITM. Suitable mass analyzer systems include two mass separators with an ion fragmentor disposed in the ion flight path between the two mass separators. Examples of suitable mass separators include, but are not limited to, quadrupoles, RF muiltipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, or combinations thereof.

Examples of suitable mass spectrometry systems for the mass analyzer include, but are not limited to, those which comprise a triple quadrupole, a quadrupole-linear ion trap, a quadrupole TOF systems, and TOF-TOF systems.

Suitable ion sources for the mass spectrometry systems include, but are not limited to, an electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. One of several desirable features of ESI is that fractions from the chromatography column can proceed directly from the column to the ESI ion source.

In various embodiments, the mass spectrometer system comprises a triple quadrupole mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can include an ion trap disposed between the ion source and the triple quadrupoles. The ion trap can be set to collect ions (e.g., all ions, ions with specific m/z ranges, etc.) and after a fill time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

In various embodiments, one or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

In various embodiments, the mass spectrometer system comprises two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

In various embodiments, the mass spectrometer system comprises two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

In various embodiments, the mass spectrometer system comprises a time-of-flight mass spectrometer and an ion reflector. The ion reflector is positioned at the end of a field-free drift region of the TOF and is used to compensate for the effects of the initial kinetic energy distribution by modifying the flight path of the ions. In various embodiments ion reflector consists of a series of rings biased with potentials that increase to a level slightly greater than an accelerating voltage. In operation, as the ions penetrate the reflector they are decelerated until their velocity in the direction of the field becomes zero. At the zero velocity point, the ions reverse direction and are accelerated back through the reflector. The ions exit the reflector with energies identical to their incoming energy but with velocities in the opposite direction. Ions with larger energies penetrate the reflector more deeply and consequently will remain in the reflector for a longer time. The potentials used in the reflector are selected to modify the flight paths of the ions such that ions of like mass and charge arrive at a detector at substantially the same time.

In various embodiments, the mass spectrometer system comprises a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In various embodiments, the mass spectrometer system comprises a tandem TOF-MS having a first, a second, and a third TOF mass separator positioned along a path of the plurality of ions generated by the pulsed ion source. The first mass separator is positioned to receive the plurality of ions generated by the pulsed ion source. The first mass separator accelerates the plurality of ions generated by the pulsed ion source, separates the plurality of ions according to their mass-to-charge ratio, and selects a first group of ions based on their mass-to-charge ratio from the plurality of ions. The first mass separator also fragments at least a portion of the first group of ions. The second mass separator is positioned to receive the first group of ions and fragments thereof generated by the first mass separator. The second mass separator accelerates the first group of ions and fragments thereof, separates the first group of ions and fragments thereof according to their mass-to-charge ratio, and selects from the first group of ions and fragments thereof a second group of ions based on their mass-to-charge ratio. The second mass separator also fragments at least a portion of the second group of ions. The first and/or the second mass separator may also include an ion guide, an ion-focusing element, and/or an ion-steering element. In various embodiments, the second TOF mass separator decelerates the first group of ions and fragments thereof. In various embodiments, the second TOF mass separator includes a field-free region and an ion selector that selects ions having a mass-to-charge ratio that is substantially within a second predetermined range. In various embodiments, at least one of the first and the second TOF mass separator includes a timed-ion-selector that selects fragmented ions. In various embodiments, at least one of the first and the second mass separators includes an ion fragmentor. The third mass separator is positioned to receive the second group of ions and fragments thereof generated by the second mass separator. The third mass separator accelerates the second group of ions and fragments thereof and separates the second group of ions and fragments thereof according to their mass-to-charge ratio. In various embodiments, the third mass separator accelerates the second group of ions and fragments thereof using pulsed acceleration. In various embodiments, an ion detector positioned to receive the second group of ions and fragments thereof. In various embodiments, an ion reflector is positioned in a field-free region to correct the energy of at least one of the first or second group of ions and fragments thereof before they reach the ion detector.

In various embodiments, the mass spectrometer system comprises a TOF mass analyzer having multiple flight paths, multiple modes of operation that can be performed simultaneously in time, or both. This TOF mass analyzer includes a path selecting ion deflector that directs ions selected from a packet of sample ions entering the mass analyzer along either a first ion path, a second ion path, or a third ion path. In some embodiments, even more ion paths may be employed. In various embodiments, the second ion deflector can be used as a path selecting ion deflector. A time-dependent voltage is applied to the path selecting ion deflector to select among the available ion paths and to allow ions having a mass-to-charge ratio within a predetermined mass-to-charge ratio range to propagate along a selected ion path.

For example, in various embodiments of operation of a TOF mass analyzer having multiple flight paths, a first predetermined voltage is applied to the path selecting ion deflector for a first predetermined time interval that corresponds to a first predetermined mass-to-charge ratio range, thereby causing ions within first mass-to-charge ratio range to propagate along the first ion path. In various embodiments, this first predetermined voltage is zero allowing the ions to continue to propagate along the initial path. A second predetermined voltage is applied to the path selecting ion deflector for a second predetermined time range corresponding to a second predetermined mass-to-charge ratio range thereby causing ions within the second mass-to-charge ratio range to propagate along the second ion path. Additional time ranges and voltages including a third, fourth etc. can be employed to accommodate as many ion paths as are required for a particular measurement. The amplitude and polarity of the first predetermined voltage is chosen to deflect ions into the first ion path, and the amplitude and polarity of the second predetermined voltage is chosen to deflect ions into the second ion path. The first time interval is chosen to correspond to the time during which ions within the first predetermined mass-to-charge ratio range are propagating through the path selecting ion deflector and the second time interval is chosen to correspond to the time during which ions within the second predetermined mass-to-charge ratio range are propagating through the path selecting ion deflector. A first TOF mass separator is positioned to receive the packet of ions within the first mass-to-charge ratio range propagating along the first ion path. The first TOF mass separator separates ions within the first mass-to-charge ratio range according to their masses. A first detector is positioned to receive the first group of ions that are propagating along the first ion path. A second TOF mass separator is positioned to receive the portion of the packet of ions propagating along the second ion path. The second TOF mass separator separates ions within the second mass-to-charge ratio range according to their masses. A second detector is positioned to receive the second group of ions that are propagating along the second ion path. In some embodiments, additional mass separators and detectors including a third, fourth, etc. may be positioned to receive ions directed along the corresponding path. In one embodiment, a third ion path is employed that discards ions within the third predetermined mass range. The first and second mass separators can be any type of mass separator. For example, at least one of the first and the second mass separator can include a field-free drift region, an ion accelerator, an ion fragmentor, or a timed ion selector. The first and second mass separators can also include multiple mass separation devices. In various embodiments, an ion reflector is included and positioned to receive the first group of ions, whereby the ion reflector improves the resolving power of the TOF mass analyzer for the first group of ions. In various embodiments, an ion reflector is included and positioned to receive the second group of ions, whereby the ion reflector improves the resolving power of the TOF mass analyzer for the second group of ions.

The following example illustrates experiments in which the absolute concentrations of multiple isoforms of cytochrome P450 in two different samples were determined in a multiplex manner. The teachings of this example are not exhaustive, and are not intended to limit the scope of these experiments or the present teachings.

Example 1

P450 Isoforms

In this example, absolute quantitation of a set of sixteen P450 isoforms is shown. This example can provide, for example, an assay for multiple P450 isoforms conductible in a single experimental run. Peptides specific to individual P450 isoforms were synthesized, labeled with a stable isotope tag (light Cleavable ICAT Reagent) and purified by HPLC to provide labeled signature peptide standard samples. These standard peptide samples were used to create a concentration curve using quantitative Multiple Reaction Monitoring (MRM) scans. Mouse liver microsome samples, control (CT) and phenobarbital induced (IND) were then labeled with heavy cleavable ICAT reagents. Phenobarbital (PB) is often used as a representative chemical for industrial solvents, pesticides, etc and is known to induce several P450 genes in subfamilies 2a, 2b, 2c and 3a. Control and Induced samples were loaded separately on the chromatographic column. Prior to loading on the chromatographic column, the control and induced samples were combined with a signature peptide internal standard sample for each signature peptide (labeled with a light cleavable ICAT reagent). Comparison of the chromatographic areas of the light (internal standard) and heavy peptide (sample) in a combined sample to the concentration curve provided quantitative information on the level of each P450 investigated in the control sample and the change in expression upon treatment with phenobarbital. Sixteen different labeled synthetic peptides, representing 16 different P450 proteins, were monitored in this experiment. The sixteen P450 proteins studied in this example are listed in column 1 of Table 1.

TABLE 1

| Protein | Signature Peptide | MRM |
|---|---|---|
| Cyp1a1 | CIGETIGR (SEQ. ID NO. 1) | 538.3/632.3 |
| Cyp1a2 | CIGEIPAK (SEQ. ID NO. 2) | 529.3/315.3 |
| Cyp1b1 | CIGEELSK (SEQ. ID NO. 3) | 553.3/662.3 |
| Cyp2a4 | YCFGEGLAR (SEQ. ID NO. 4) | 621.8/749.4 |
| Cyp2a12 | FCLGESLAK (SEQ. ID NO. 5) | 590.8/703.4 |
| Cyp2b10 | ICLGESIAR (SEQ. ID NO. 6) | 594.8/745.4 |
| Cyp2c29/Cyp2c37 | ICAGEGLAR (SEQ. ID NO. 7) | 558.8/673.4 |
| Cyp2c39 | VCAGEGLAR (SEQ. ID NO. 8) | 551.8/673.4 |

TABLE 1-continued

| Protein | Signature Peptide | MRM |
| --- | --- | --- |
| Cyp2c40 | ICVGESLAR (SEQ. ID NO. 9) | 587.8/731.4 |
| Cyp2d9 | SCLGEALAR (SEQ. ID NO. 10) | 573.8/729.4 |
| Cyp2d22/Cyp2d26 | SCLGEPLAR (SEQ. ID NO. 11) | 586.8/642.4 |
| Cyp2e1 | VCVGEGLAR (SEQ.ID NO. 12) | 565.8/701.4 |
| Cyp2f2 | LCLGEPLAR (SEQ. ID NO. 13) | 599.8/642.4 |
| Cyp2j5 | ACLGEQLAK (SEQ. ID NO. 14) | 580.3/758.4 |
| Cyp3a11 | NCLGMR (SEQ. ID NO. 15) | 460.7/363.2 |
| Cyp4a10/Cyp4a14 | NCIGK (SEQ. ID NO. 16) | 381.2/204.1 |

The materials and method used in this example were substantially as follows.

Selection, Preparation and Quantitation of Labeled Synthetic Peptide Standards

The protein sequences of all members of the P450 protein family used in this experiment were examined. Tryptic peptide sequences containing cysteine residues were found which uniquely identified each protein isoform. Synthetic peptides of these sequences were made and labeled with CO cleavable ICAT® reagent. Peptides were synthesized using Fmoc chemistry (Applied Biosystems 433A Peptide Synthesizer, Applied Biosystems, Inc. Foster City, Calif.), derivatized using the cleavable ICAT® reagent, purified by HPLC, and their concentration quantified by amino acid analysis (Applied Biosystems 421A Derivatizer). The sixteen P450 isoforms of this experiment are listed in column 1 of Table 1. Column 2 of Table 1 list the signature peptide selected for the corresponding P450 isoform in this experiment.

Mass Analyzer System

A liquid chromatography (LC) mass spectrometry (MS) system was used to analyze the standard samples and unknown samples from both control and phenobarbital induced mice. Samples were separated by reverse phase HPLC on a C18 Genesis AQ column (75 μm×10 cm, Vydac) using a 10 minute gradient (15-45% acetonitrile in 0.1% formic acid). MRM analysis was performed using a MS system with a NanoSpray™ source on a 4000 Q TRAP® system (Applied Biosystems, Inc., Foster City, Calif.) (Q1-3 Dalton (Da) mass window, Q3-1 Da mass window). A simplified schematic diagram of the mass spectrometer system used is shown in FIG. 2.

Figure 2:
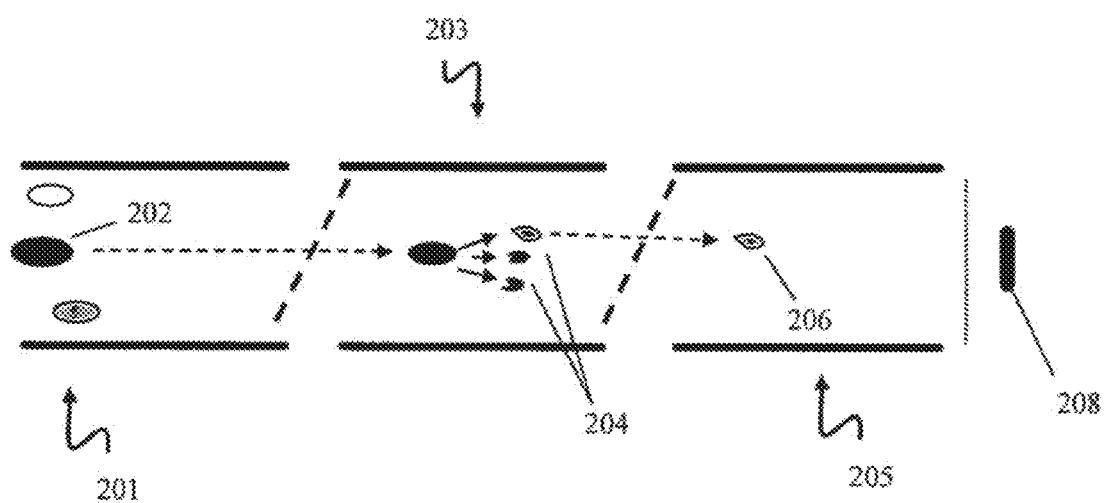
FIG. 2 is a simplified schematic diagram of the mass spectrometer system used in Examples 1 and 2.

Referring to FIG. 2, a MRM scan can be conducted, for example, by setting the first mass separator 201 (in the instrument used the first mass separator is a quadrupole) to transmit the signature peptide of interest (i.e., the parent ion 202, e.g., by setting the first mass separator to transmit ions in a mass window about 3 mass units wide substantially centered on the mass of a signature peptide). In various embodiments, the collision energy can be selected to facilitate producing the selected diagnostic charged fragment of this peptide (the selected diagnostic daughter ion) in the ion fragmentor (here the ion fragmentor comprises a collision gas for conducting CID and a quadrupole 203, to facilitate, e.g., collecting ion fragments 204 and fragment ion transmittal); and the second mass separator 205 (in the instrument used the second mass separator is a quadrupole configurable as a linear ion trap) is set to transmit the diagnostic daughter ion (or ions) 206 of interest (e.g., by setting the second mass separator to transmit ions in a mass window about 1 mass unit wide substantially centered on the mass of a diagnostic daughter ion) to a detector 208 to generate an ion signal for the diagnostic daughter ion (or ions) transmitted. In these experiments the second mass separator was operated in quadrupole mode.

MRM parameters, for each signature peptide, were chosen to facilitate optimizing the signal for the selected diagnostic daughter ion (or ions) associated with that signature peptide. The dwell times (25-100 ms) used on the mass separators in this experiment and the ability to rapidly change between MRM transitions allowed multiple components in a mixture to be monitored in a single LC-MS run. Although dwell times between about 25-100 ms were used in these experiments, dwell times between about 10 ms to about 200 ms could be used depending on experimental conditions. For example, 50-100 different components can be monitored in a single LC-MS run. The parent ion m/z and daughter ion m/z MRM settings (these settings do not assume passing singly charged ions) for each signature peptide are given in column 3 of Table 1 and the approximate retention time on the column (in minutes) for each signature peptide is given in column 4 of Table 1.

Generation of Concentration Curve

Figure 3:
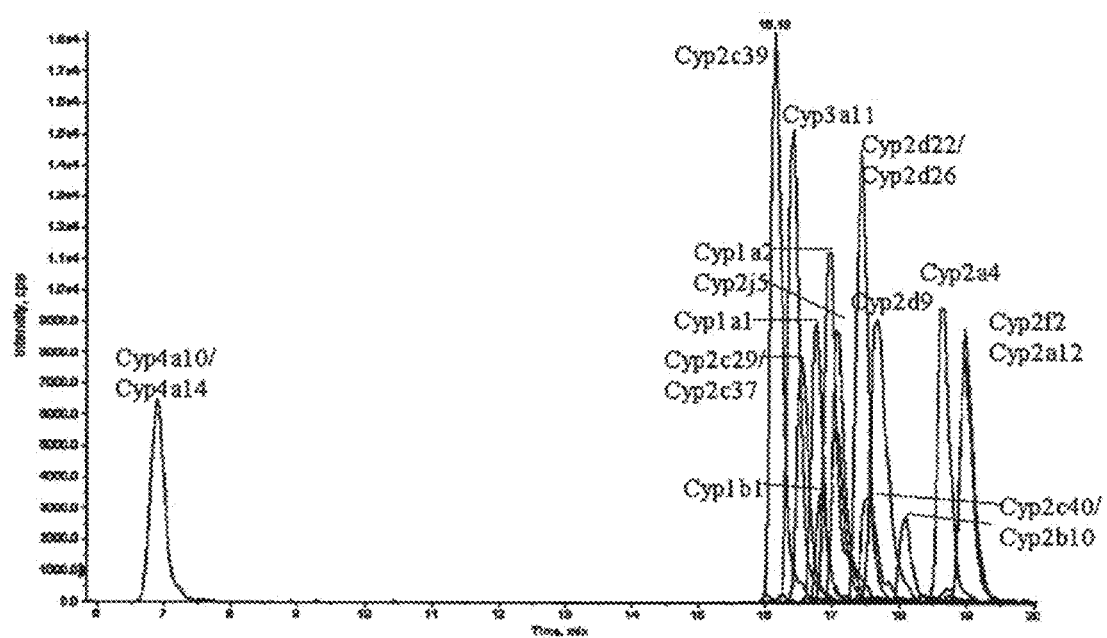
FIG. 3 is a MRM chromatogram of 3.2 fmol on column of each labeled synthetic signature peptide of Examples 1 and 2.

In this example, an MRM assay was developed to quantify and create concentration curves for a set of 16 synthetic peptides in a single run, using light ICAT® reagent labeled forms of the peptides. Using a dwell time of 45 ms and monitoring 40 different transitions, the cycle time was only 2 seconds. A 10 minute gradient from 15-35% acetonitrile was used to separate the P450 peptides in time. A resultant MRM chromatogram for 3.2 fmol of each signature peptide on column is shown in FIG. 3. The y-axis in FIG. 3 corresponds to the mass spectrometry system detector signal (in counts per second (cps)) of the diagnostic daughter ion corresponding to the signature peptide of the P450 proteins noted in FIG. 3. The x-axis corresponds to the retention time (in minutes) of the signature peptide in the LC portion of the system. The chromatograms in FIG. 3 are labeled according to the P450 isoform to which they correspond. Notice that the MRM response varies for the different signature peptide sequences.

The signature peptide standard samples were used to generate the concentration curves for each peptide and act as an internal standard when measuring the unknown samples.

Figure 4:
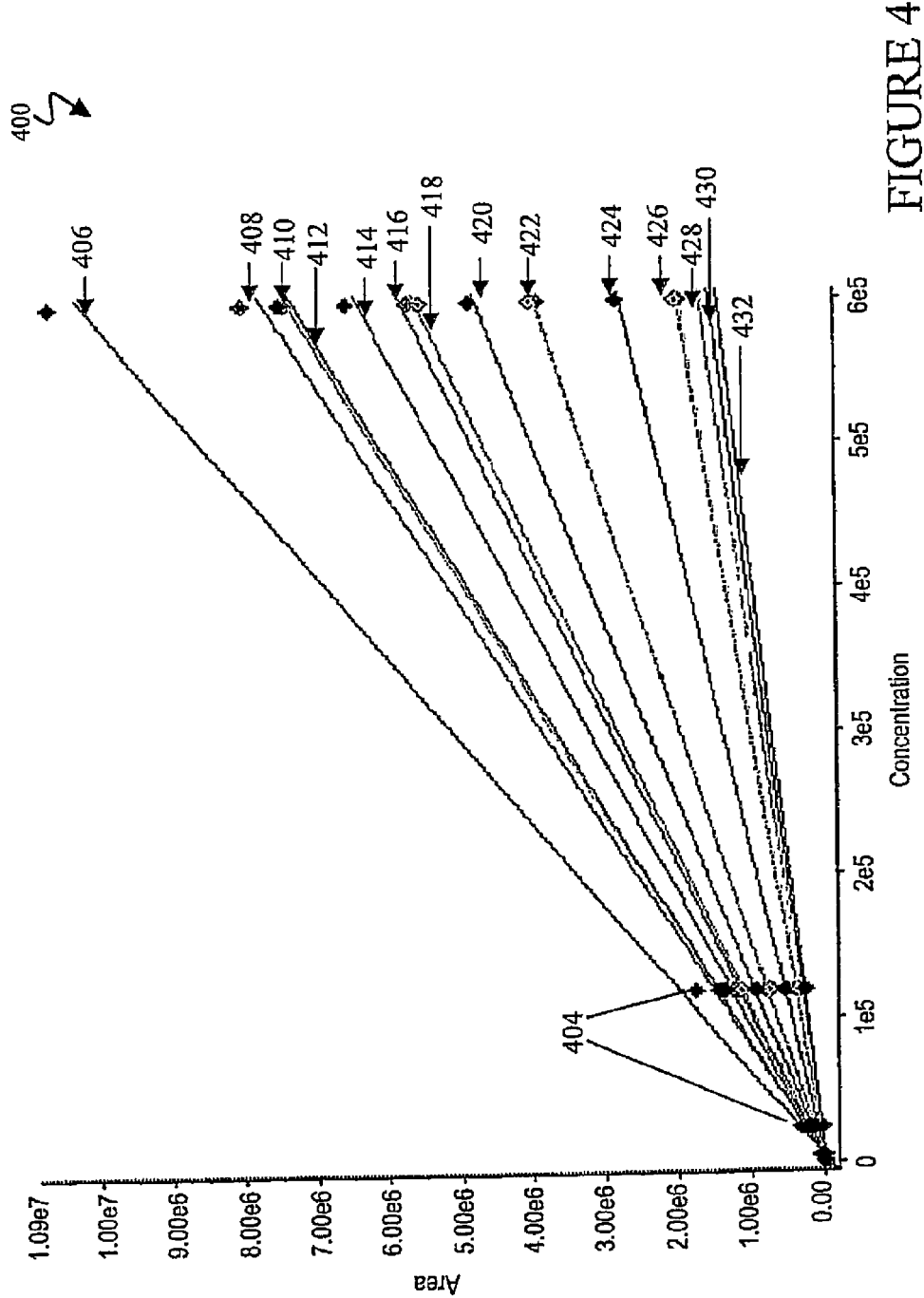
FIG. 4 is a concentration curve generated for the diagnostic daughter ion of the ICLGESIAR peptide (the signature peptide chosen for the Cyp2b10 isoform of P450) of Examples 1 and 2.

Concentration curves were measured for each synthetic light ICAT® reagent labeled peptide. The concentration curves were generated in the presence of heavy ICAT® reagent labeled microsomal proteins, to control for background and ion suppression. Examples of concentration curves generated in this experiment are shown in FIG. 4 as a plot of the diagnostic daughter ion signal area (y-axis) as a function of the signature peptide concentration (femtomoles on column) (x-axis). FIG. 4 shows concentration curves 400 for the diagnostic daughter ions of various signature peptides chosen for the various P450 isoforms in this experiment, where the filled symbols 404 represent the experimental measurements. Examples, of concentration curves for the isoforms: Cyp2d9 406, Cyp1a1 408, Cyp2b10 410, Cyp2j5 412, Cyp2d22/Cyp2d26 414, Cyp3a11 416, Cyp1b1 418, Cyp2f2 420, Cyp2a12 422, Cyp2c29/Cyp2c37 424, Cyp4a10/Cyp4a14 426, Cyp2c39 428, Cyp1a2 430, Cyp2a4 432, and Cyp2d9 432, are shown.

Labeling of Mouse Liver Microsomes

The proteins from mouse liver microsomes were extracted and the protein extracts were labeled with heavy cleavable ICAT® reagent and samples were processed according to a standard Applied Biosystems ICAT® brand reagent kit protocol (e.g., Applied Biosystems Part No. 4333373Rev.A).

Quantitation of Expression

The absolute expression of a P450 isoform of this experiment, for both control (CT) and induced IND samples, can be determined, for example, by comparing the MRM peak area from the control sample with the concentration curve for the corresponding signature peptide-diagnostic daughter ion transition.

Table 2 shows the concentration ratios obtained for the sixteen P450 isoforms investigated in this experiment. In Table 2: column 1 lists the P450 isoform; column 2 lists the signature peptide selected for that isoform; column 3 gives the absolute amount of the P450 isoform expressed by the control samples in the experiment in units of femtomoles per microgram (μg) of microsomal protein; column 4 gives the ratio of induced (IND) to control (CT) expression; and column 5 qualitatively indicates whether the protein was upregulated in the ND samples relative to CT and columns 6 and 7 show respectively, the upper and lower limits of the 95% confidence intervals of the corresponding entry in column 4. In various embodiments, one or more proteins in the sample known to be unchanging (e.g., in these experiments using liver microsomes a liver protein) will be selected and signature peptide-diagnostic daughter ion transition of one or more of these proteins used provide a normalization factor between control and experimental samples.

The basal level of expression of each protein in control mouse liver microsomes was measured, and the proteins monitored showed a range of basal expression from about 1.38 to about 55.84 fmol/μg of microsomal protein. The microsomal proteins from mice, which were treated with phenobarbital, were also studied and the changes in expression of each protein in response to the drug were determined. The ratios from 4 separate experiments were averaged and the 95% confidence intervals calculated. Good reproducibility was obtained across experiments, as shown by the narrow 95% CI values. The P450 protein, Cyp2b10, showed an increase in expression upon drug treatment of about 6-fold over control. Cyp2c29/Cyp2c37 and Cyp3a11 also showed a small increase in expression, about 3-fold, whereas Cyp2d9 showed a slight decrease in expression.

TABLE 2

| Protein | Signature Peptide | [CT] fmol/μg | IND/CT | Change | Upper CI | Lower CI |
|---|---|---|---|---|---|---|
| Cyp1a1 | CIGETIGR (SEQ. ID NO. 1) | 5.38 | 1.03 | | 1.09 | 0.97 |
| Cyp1a2 | CIGEIPAK (SEQ. ID NO. 2) | 1.38 | 0.91 | | 0.95 | 0.87 |
| Cyp1b1 | CIGEELSK (SEQ. ID NO. 3) | 4.11 | 1.08 | | 1.23 | 0.96 |
| Cyp2a4 | YCFGEGLAR (SEQ. ID NO. 4) | 0.51 | 1.53 | 1.19 | 1.33 | 1.06 |
| Cyp2a12 | FCLGESLAK (SEQ. ID NO. 5) | 1.61 | 5.07 | 1.0 | 1.07 | 0.93 |
| Cyp2b10 | ICLGESIAR (SEQ. ID NO. 6) | 2.41 | 1.41 6.07 | up | 7.24 | 5.08 |
| Cyp2c29/Cyp2c37 | ICAGEGLAR (SEQ. ID NO. 7) | 55.84 | 3.5 3.06 | up | 3.53 | 2.65 |
| Cyp2c39 | VCAGEGLAR (SEQ. ID NO. 8) | 7.58 | 0.99 | | 1.05 | 0.94 |
| Cyp2c40 | ICVGESLAR (SEQ. ID NO. 9) | 3.81 | 6.15 1.50 | 0.98 | 1.03 | 0.93 |
| Cyp2d9 | SCLGEALAR (SEQ. ID NO. 10) | 12.42 | 0.80 | 0.61 down | 0.70 | 0.52 |
| Cyp2d22/Cyp2d26 | SCLGEPLAR (SEQ. ID NO. 11) | 6.12 | 1.68 | 10.90 | 0.96 | 0.86 |
| Cyp2e1 | VCVGEGLAR (SEQ. ID NO. 12) | 35.13 | 0.86 | | 0.91 | 0.82 |
| Cyp2f2 | LCLGEPLAR (SEQ. ID NO. 13) | 21.74 | 0.75 | | 0.78 | 0.72 |
| Cyp2j5 | ACLGEQLAK (SEQ. ID NO. 14) | 0.33 | 9.05 | 10.98 | 1.02 | 0.93 |
| Cyp3a11 | NCLGMR (SEQ. ID NO. 15) | *5.48 | 3.57 | | 3.94 | 3.23 |

TABLE 2-continued

| Protein | Signature Peptide | [CT] fmol/µg | IND/ CT | Change | Upper CI | Lower CI |
|---|---|---|---|---|---|---|
| Cyp4a10/Cyp4a14 | NCIGK (SEQ. ID NO. 16) | 2.32.71 | 11.61 | | 1.97 | 1.31 |

Example 2

P450 Isoforms

In this example, absolute quantitation of a set of sixteen P450 isoforms is shown where the control and induce samples were combined (without the addition of signature peptide internal standard samples) and loaded on to the chromatographic column. This example can also provide, for example, an assay for multiple P450 isoforms conductible in a single experimental run. This example used a portion of the same control and induced samples, before said samples were labeled, used in Example 1. The labeled signature peptide samples used in Example 2 were the same samples used in Example 1.

In Example 2, mouse liver microsome samples, control (CT) and phenobarbital induced (IND) were then labeled, respectively, with light cleavable and heavy cleavable ICAT® reagents. Comparison of the chromatographic areas of the light and heavy peptide in a sample to the concentration curve provided quantitative information on the level of each P450 investigated in the control sample and the change in expression upon treatment with phenobarbital. Sixteen different labeled synthetic peptides, representing 16 different P450 proteins, were monitored in this experiment. The sixteen P450 proteins studied in this Example 2 are listed in column 1 of Table 1. Column 2 of Table 1 list the signature peptide selected for the corresponding P450 isoform in this experiment.

The materials and method used in this example were substantially the same as those used in Example 1 except as follows.

Mass Analyzer System

A liquid chromatography (LC) mass spectrometry (MS) system was used to analyze the standard samples and unknown samples from both control and phenobarbital induced mice. Control and Induced samples were combined, digested, and loaded onto the chromatographic column as a combined sample. Signature peptide internal standard samples were not added to this combined sample. Samples were separated by reverse phase HPLC on a C18 Genesis AQ column (75 µm×10 cm, Vydac) using a 10 minute gradient (15-45% acetonitrile in 0.1% formic acid). MRM analysis was performed as described in Example 1.

Generation of Concentration Curve

The same concentration curves described in Example 1 were used in this Example 2.

Labeling of Mouse Liver Microsomes

The proteins from mouse liver microsomes were extracted and the protein extracts were labeled with cleavable ICAT® reagent (heavy for the IND, and light for the CT) and samples were processed according to a standard Applied Biosystems ICAT® brand reagent kit protocol (e.g., Applied Biosystems Part No. 4333373Rev.A).

Quantitation of Expression

Figure 5:
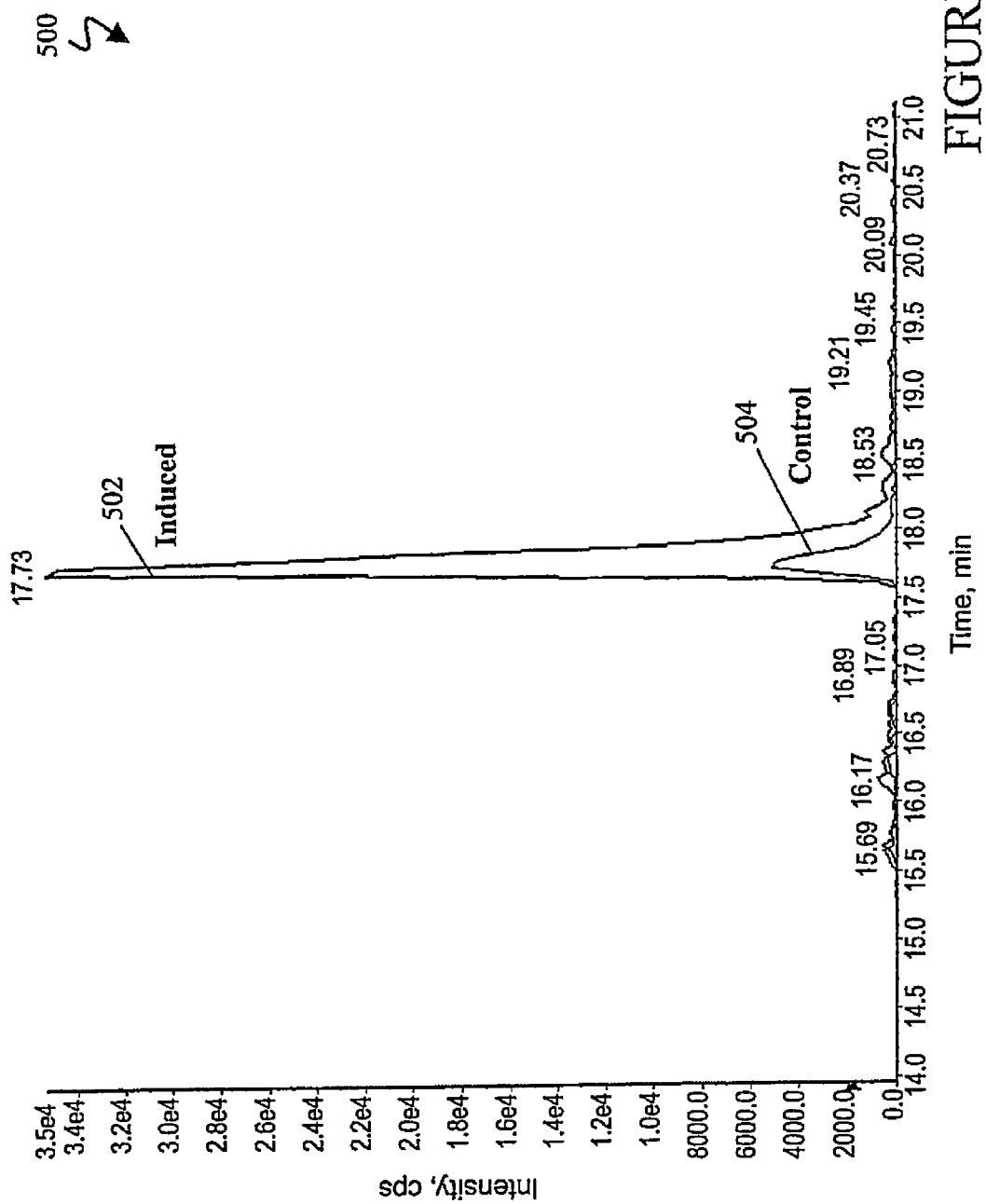
FIG. 5 is a MRM chromatogram for the diagnostic daughter ion of the ICLGESIAR peptide (the signature peptide chosen for the Cyp2b10 isoform of P450) of Example 1, for both control and phenobarbital induced samples.

The absolute expression of a P450 isoform of this experiment, for both CT and IND samples, can be determined, for example, by comparing the MRM peak area from the control sample with the concentration curve for the corresponding signature peptide-diagnostic daughter ion transition. For example, FIG. 5 shows a MRM chromatogram 500 for the diagnostic daughter ion of the ICLGESIAR (SEQ. ID NO. 6) peptide (the signature peptide chosen for the Cyp2b10 isoform of P450) of Example 2, with signals from both control 502 and phenobarbital induced 504 samples. The concentration of the ICLGESIAR (SEQ. ID NO. 6) peptide in the CT and IND samples, and therefore the corresponding specific P450 isoform in the CT and IND samples, can be determined, for example, by comparing the MRM peak area from the control sample signal 502 with the corresponding concentration curve (e.g., FIG. 4) generated from the synthetic peptides. For example, in the control liver microsomes of this experiment, Cyp2b10 was expressed at about 2.4 fmol/µg of microsomal protein. Further, comparing the concentrations calculated from the concentration curve for the ICLGESIAR (SEQ. ID NO. 6) peptide from the induced sample signal 504 and the control sample signal 502, or comparing the MRM peak area for each, indicates that the expression of P450 Cyp2b10 isoform is upregulated about 7 fold upon treatment with phenobarbital.

Figure 6:
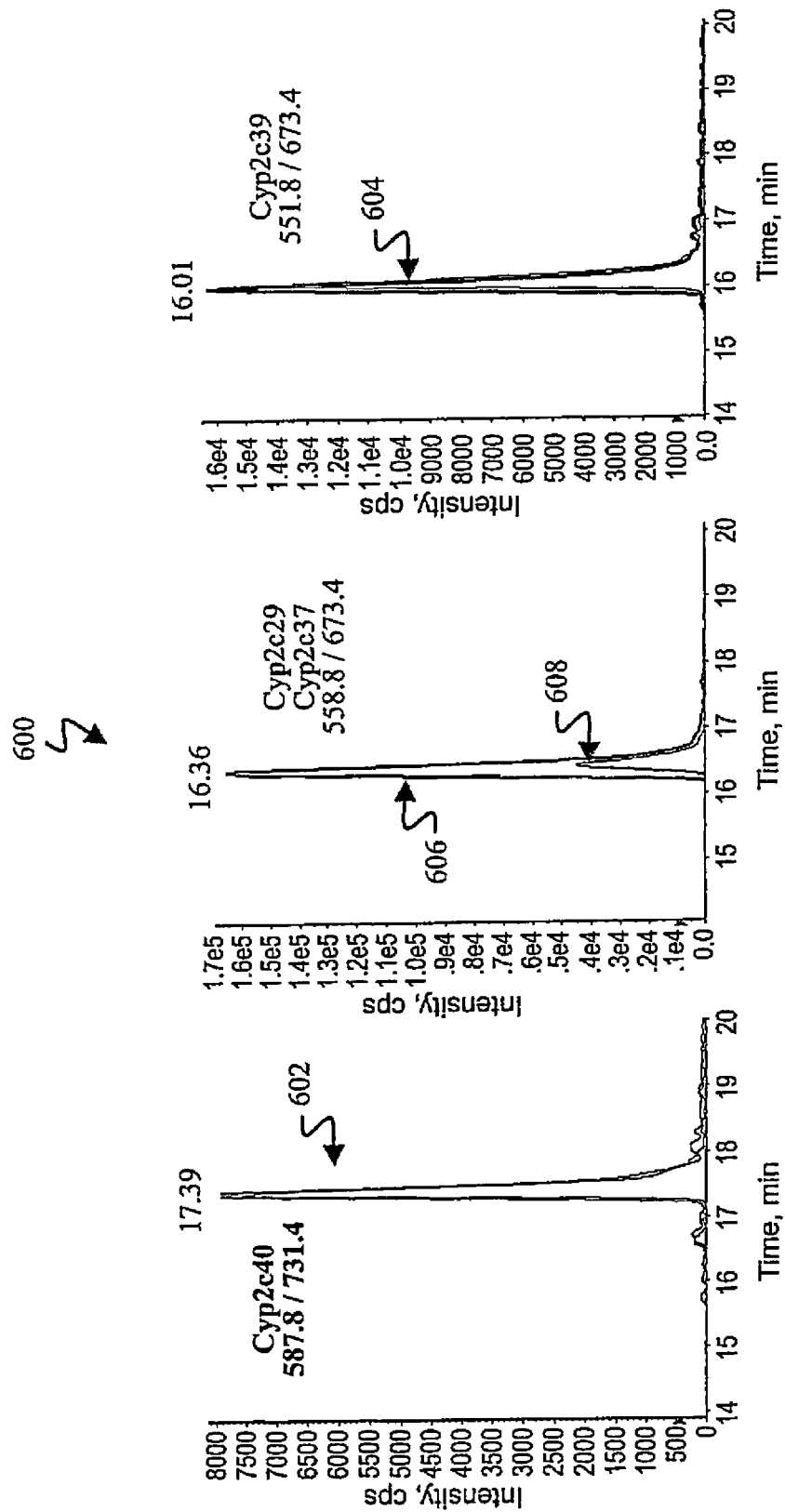
FIG. 6 shows MRM scan data for the quantitation of P450 proteins within the same subfamily.

In various, embodiments, changes in expression of highly homologous proteins within the same subfamily can be determined. For example, four isoforms from the Cyp2C subfamily (Cyp2c40, Cyp2c29, Cyp2c37 and Cyp2c39) have approximately 80% sequence homology. In various embodiments, individual quantitation information can be obtained using, e.g., the specificity of the MRM method. Referring to FIG. 6, shown are MRM chromatograms 600 of control and phenobarbital induced samples, two of the isoforms (Cyp2c40 602 and Cyp2c39 604) were not substantially inducible by phenobarbitol. However, the Cyp2c29/Cyp2c37 70 isoforms showed about a 3 fold increase in expression of the induced sample 606 over the control sample 608 based on the MRM peak areas.

In various embodiments, to account for, e.g., small experimental variation in amounts of protein starting material or sample preparation, one or more proteins can be chosen to act as normalization proteins. Proteins chosen to serve as normalizations factors should remain unchanged regardless of the method of induction (e.g., drug induction) and peptide fragments of these proteins should be observed after routine sample preparation to serve as internal standards within the experiment.

Table 3 shows the normalization proteins and signature peptides used in the quantitation of P450 isozymes in Example 2. In various embodiments, normalization proteins are microsomal. In various embodiments, signature peptides of the normalization proteins are isolated tryptic fragments. In various embodiments, signature peptides are in the range between about 4 to about 30 amino acid residues in length, or between about 6 to about 15 amino acid residues in length, or between about 16 to about 30 amino acid residues in length or between about 8 to about 16 amino acid residues in length or between about 10 to about 15 amino acid residues in length.

TABLE 3

| Protein | Signature Peptide | MRM | Avg | Upper CI | Lower CI |
|---|---|---|---|---|---|
| Corticosteroid 11 beta-dehydrogenase isozyme 1 | EECALEIIK (SEQ. ID NO. 25) | 637.8/686.4 | 1.02 | 1.07 | 0.97 |
| Triglyeride transfer protein | GCPSLAEHWK (SEQ. ID NO. 26) | 677.8/967.5 | 1.02 | 1.16 | 0.94 |
| Microsomal GST | VFANPEDCAFGK (SEQ. ID NO. 27) | 791.4/1150.5 | 1.03 | 1.17 | 0.91 |
| Microsomal GST | VFANPEDCAFGK (SEQ. ID NO. 27) | 527.9/575.8 | 1.03 | 1.21 | 0.86 |

Figure 7:
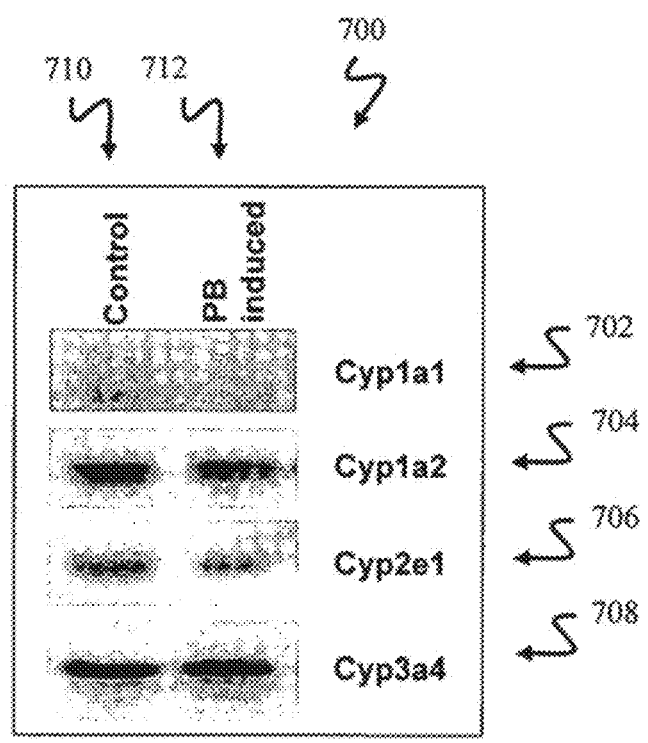
FIG. 7 illustrates the results of a Western blot analysis of four of the subfamilies of P450 proteins: Cyp1a1, Cyp1a2, Cyp2e1 and Cyp3a4.

FIG. 7 illustrates the results of a Western blot analysis 700 of four of the subfamilies of P450 proteins: Cyp1a1 702, Cyp1a2 704, Cyp2e1 706 and Cyp3a4 708. Commercially available antibodies to four of the subfamilies of P450 proteins were obtained and used to analyze expressed protein levels in both the control 710 and phenobarbital induced 712 samples. Very little of the Cyp1a1 protein was observed in either sample. Cyp1a2, Cyp2e1 and Cyp3a4 proteins were observed in both samples at similar levels of expression.

While the teachings have been particularly shown and described with reference to specific illustrative embodiments, it should be understood that various changes in form and detail may be made without departing from the spirit and scope of the teachings. For example, any of the various disclosed labeling approaches, PDITM approaches, concentration curves, and mass analyzer systems and can be combined to provide a method for determining the absolute concentration of a protein, or multiple proteins, in a sample or multiple samples. Therefore, all embodiments that come within the scope and spirit of the teachings, and equivalents thereto are claimed. The descriptions and diagrams of the methods, systems, and assays of the present teachings should not be read as limited to the described order of elements unless stated to that effect.

What is claimed is:

1. A method for determining the concentration of one or more proteins of interest in two or more samples of interest using parent-daughter ion transition monitoring (PDITM) in mass spectrometry, comprising the steps of:
    providing an internal standard sample for each of the one or more proteins of interest, each internal standard sample comprising a signature peptide having a sequence that uniquely identifies each corresponding protein of interest;
    labeling the signature peptide with a chemical moiety comprising either
        a) a heavy or light isotopic tag
        or
        b) an isobaric tag
        to generate a labeled internal standard sample comprising a labeled signature peptide for each protein of interest, wherein each labeled signature peptide, when ionized, is referred to as a parent ion;
    subjecting the labeled internal standard sample to PDITM;
    selecting a diagnostic daughter ion for each labeled signature peptide;
    labeling the one or more proteins of interest in two or more samples of interest, separately, with the chemical moiety comprising either
        a) the other of the heavy or light isotopic tag as compared to the isotopic tag of the labeled internal standard sample
        or
        b) an isobaric tag having the same mass but a different signal following PDITM as compared to the isobaric tag of the labeled internal standard sample,
    to generate two or more labeled samples of interest, the two or more labeled samples of interest thereby being differentially labeled with respect to the labeled internal standard sample;
    combining, to produce two or more combined samples, at least a portion of the one or more labeled internal standard samples with at least a portion of each of two or more differentially labeled samples of interest;
    loading at least a portion of each combined sample on a chromatographic column;
    eluting at least a portion of the combined sample from the chromatographic column to generate an eluent containing signature peptides wherein heavy and light signature peptides are co-eluting or wherein isobaric tagged signature peptides are co-eluting, respectively;
    subjecting at least a portion of the eluent from the chromatographic column to PDITM, wherein (i) a transmitted parent ion m/z range of each PDITM scan includes a m/z value of one or more of the labeled signature peptides and (ii) a transmitted daughter ion m/z range of each PDITM scan includes a m/z value of one or more of the selected diagnostic daughter ions corresponding to the transmitted labeled signature peptide;
    measuring the ion signal of one or more of the selected diagnostic daughter ions using said PDITM; and
    determining the concentration of one or more proteins of interest in the two or more samples of interest by comparing the measured ion signal of a selected diagnostic daughter ion corresponding to the protein of interest from a sample of interest to the measured ion signal for the selected diagnostic daughter ion corresponding to the protein of interest from a labeled internal standard sample
    wherein, optionally, the combining step is preceded, followed, or both preceded and followed by digesting protein of each sample or of the combined sample to generate peptides.

2. The method of claim 1, wherein the step of selecting a diagnostic daughter ion for each labeled signature peptide comprises selecting the diagnostic daughter ion based on one or more of level of detection (LOD), limit of quantitation (LOQ), linearity of quantitation over a specific dynamic range of concentrations, and combinations thereof.

3. The method of claim 1, wherein the chemical moiety comprises a heavy or light isotopic tag and the isotopic tag comprises an isotopically coded affinity tag.

4. The method of claim 1, wherein the chemical moiety comprises an isobaric tag.

5. The method of claim 1, wherein the chemical moiety comprises a heavy or light isotopic tag and the isotopic tag is a mass differential tag.

6. The method of claim 1, wherein the two or more samples of interest are derived from a biological system that has been exposed to a chemical agent; and the concentration of said proteins of interest is an assessment of a response of the biological system to the chemical agent.

7. The method of claim 6, wherein the chemical agent comprises a pharmaceutical agent.

8. The method of claim 7, wherein the biological system comprises a biological process.

9. The method of claim 1, wherein the one or more proteins of interest in the two or more samples of interest is derived from a biological system being in a disease state and the concentrations of the one or more proteins of interest in the two or more samples of interest is diagnostic or prognostic of the disease state.

10. The method of claim 9, wherein the biological system comprises a biological process.

11. The method of claim 1, wherein the internal standard sample for each of the one or more proteins of interest comprises a pooled reference sample.

12. The method of claim 1, wherein the combining step is followed by the step of subjecting at least a portion of the two or more combined samples to digestion to produce digested combined samples prior to the loading step, and wherein the portion of each combined sample loaded on a chromatographic column is all or a portion of each digested combined sample.

13. The method of claim 12, wherein the digestion comprises chemical digestion.

14. The method of claim 12, wherein the digestion comprises enzymatic digestion.

15. The method of claim 1, wherein one or more of the standard samples are subjected to a digestion prior to the combining step.

16. The method of claim 15, wherein the digestion comprises chemical digestion.

17. The method of claim 15, wherein the digestion comprises enzymatic digestion.

18. The method of claim 1, wherein, in the combining step, the portion of the one or more labeled standard samples is a known concentration, and the step of determining the concentration of one or more proteins of interest comprises determining the absolute concentration of the protein of interest.

19. The method of claim 1, the step of determining the concentration of a protein of interest comprises determining the relative concentration of the protein of interest, wherein the labeled standard sample comprises a pooled reference sample.

20. A method for determining the relative concentration of one or more proteins of interest in two or more samples of interest, using parent-daughter ion transition monitoring (PDITM) in mass spectrometry, comprising the steps of:

provmg an internal standard sample comprising a portion of each sample of interest, the internal standard sample comprising a signature peptide having a sequence that uniquely identifies each corresponding protein of interest;

labelling the internal standard sample with a chemical moiety comprising either a) a heavy or light isotopic tag, or b) an isobaric tag, to generate a labeled internal standard sample comprising a labeled signature peptide for each protein of interest, wherein each labeled signature peptide, when ionized, is referred to as a parent ion:

subjecting the labeled internal standard sample to PDITM;

selecting a diagnostic daughter ion for each labeled signature peptide for each protein of interest;

labeling the one or more proteins of interest in two or more samples of interest, separately, with the chemical moiety comprising either a) the other of the heavy or light isotopic tag as compared to the isotopic tag of the labeled internal standard sample or b) an isobaric tag having the same mass but a different signal following PDITM as compared to the isobaric tag of the labeled internal standard sample, to generate two or more labeled samples of interest, the two or more labeled samples of interest thereby being differentially labeled with respect to the labeled internal standard sample;

combining, to produce two or more combined samples, at least a portion of the labeled internal standard sample with at least a portion of each of two or more differentially labeled samples of interest;

loading at least a portion of each combined sample on a chromatographic column;

eluting at least a portion of each combined sample from the chromatographic column to generate an eluent containing signature peptides wherein heavy and light signature peptides are co-eluting or wherein isobaric tagged signature peptides are co-eluting, respectively;

subjecting at least a portion of the eluent from the chromatographic column for each combined sample to PDITM, wherein (i) a transmitted parent ion m/z range of each PDITM scan includes a m/z value of one or more of the labeled signature peptides and (ii) a transmitted daughter ion m/z range of each PDITM scan includes a m/z value of one or more of the selected diagnostic daughter ions corresponding to the transmitted labeled signature peptide, measuring the ion signal of one or more of the selected diagnostic daughter ions using said PDITM; and determining the concentration of a protein of interest in one or more of the samples of interest relative to the concentration of the protein of interest in the internal standard sample by comparing the measured ion signal of a selected diagnostic daughter ion corresponding to the protein of interest in one or more of the samples of interest to the measured ion signal for the selected diagnostic daughter ion corresponding to the protein of interest from the labeled internal standard sample wherein, optionally, the combining step is preceded, followed, or both preceded and followed by digesting protein of each sample or of the combined sample to generate peptides.

* * * * *

```
                      SEQUENCE LISTING

<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: synthetic construct

<400> SEQUENCE: 1

Cys Ile Gly Glu Thr Ile Gly Arg
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic construct

<400> SEQUENCE: 2

Cys Ile Gly Glu Ile Pro Ala Lys
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Cys Ile Gly Glu Glu Leu Ser Lys
```

```
<210> SEQ ID NO 4
<211> LENGTH: 9
<212> TYPE: PRT
<213> ORGANISM: Artificial Sequence
<220> FEATURE:
<223> OTHER INFORMATION: synthetic construct

<400> SEQUENCE: 4

Tyr Cys Phe Gly Glu Gly Leu Ala Arg
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic construct

<400> SEQUENCE: 5

Phe Cys Leu Gly Glu Ser Leu Ala Lys
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic construct

<400> SEQUENCE: 6

Ile Cys Leu Gly Glu Ser Ile Ala Arg
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic construct

<400> SEQUENCE: 7

Ile Cys Ala Gly Glu Gly Leu Ala Arg
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic construct

<400> SEQUENCE: 8

Val Cys Ala Gly Glu Gly Leu Ala Arg
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic construct

<400> SEQUENCE: 9

Ile Cys Val Gly Glu Ser Leu Ala Arg
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: synthetic construct

<400> SEQUENCE: 10

Ser Cys Leu Gly Glu Ala Leu Ala Arg
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic construct

<400> SEQUENCE: 11

Ser Cys Leu Gly Glu Pro Leu Ala Arg
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic construct

<400> SEQUENCE: 12

Val Cys Val Gly Glu Gly Leu Ala Arg
1               5

<210> SEQ ID NO 13
<211> LENGTH: 9
<212> TYPE: PRT
<213> ORGANISM: Artificial Sequence
<220> FEATURE:
<223> OTHER INFORMATION: synthetic construct

<400> SEQUENCE: 13

Leu Cys Leu Gly Glu Pro Leu Ala Arg
1               5

<210> SEQ ID NO 14
<211> LENGTH: 9
<212> TYPE: PRT
<213> ORGANISM: Artificial Sequence
<220> FEATURE:
<223> OTHER INFORMATION: synthetic construct

<400> SEQUENCE: 14

Ala Cys Leu Gly Glu Gln Leu Ala Lys
1               5

<210> SEQ ID NO 15
<211> LENGTH: 6
<212> TYPE: PRT
<213> ORGANISM: Artificial Sequence
<220> FEATURE:
<223> OTHER INFORMATION: synthetic construct

<400> SEQUENCE: 15

Asn Cys Leu Gly Met Arg
1               5

<210> SEQ ID NO 16
```

```
<211> LENGTH: 5
<212> TYPE: PRT
<213> ORGANISM: Artificial Sequence
<220> FEATURE:
<223> OTHER INFORMATION: synthetic construct

<400> SEQUENCE: 16

Asn Cys Ile Gly Lys
1               5

<210> SEQ ID NO 17
<211> LENGTH: 18
<212> TYPE: PRT
<213> ORGANISM: Artificial Sequence
<220> FEATURE:
<223> OTHER INFORMATION: synthetic construct

<400> SEQUENCE: 17

Tyr Ile Asp Leu Leu Pro Thr Ser Leu Pro His Ala Val Thr Cys Asp Ile Lys
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: synthetic construct

<400> SEQUENCE: 18

Ile Cys Val Gly Glu Gly Leu Ala Arg
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic construct

<400> SEQUENCE: 19

Ala Cys Leu Gly Glu Pro Leu Ala Arg
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic construct

<400> SEQUENCE: 20

Cys Ile Gly Glu Val Leu Ala Lys
1               5

<210> SEQ ID NO 21
<211> LENGTH: 11
<212> TYPE: PRT
<213> ORGANISM: Artificial Sequence
<220> FEATURE:
<223> OTHER INFORMATION: synthetic construct

<400> SEQUENCE: 21

Gly Phe Cys Met Phe Asp Met Glu Cys His Lys
1               5                   10

<210> SEQ ID NO 22
<211> LENGTH: 9
<212> TYPE: PRT
```

<213> ORGANISM: Artificial Sequence
<220> FEATURE:
<223> OTHER INFORMATION: synthetic construct

<400> SEQUENCE: 22

Ile Cys Leu Gly Glu Gly Ile Ala Arg
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic construct

<400> SEQUENCE: 23

Leu Cys Gln Asn Glu Gly Cys Lys
1               5

<210> SEQ ID NO 24
<211> LENGTH: 10
<212> TYPE: PRT
<213> ORGANISM: Artificial Sequence
<220> FEATURE:
<223> OTHER INFORMATION: synthetic construct

<400> SEQUENCE: 24

Gly Cys Pro Ser Leu Ser Glu Leu Trp Arg
1               5                   10

<210> SEQ ID NO 25
<211> LENGTH: 9
<212> TYPE: PRT
<213> ORGANISM: Artificial Sequence
<220> FEATURE:
<223> OTHER INFORMATION: synthetic construct

<400> SEQUENCE: 25

Glu Glu Cys Ala Leu Glu Ile Ile Lys
1               5

<210> SEQ ID NO 26
<211> LENGTH: 10
<212> TYPE: PRT
<213> ORGANISM: Artificial Sequence
<220> FEATURE:
<223> OTHER INFORMATION: synthetic construct

<400> SEQUENCE: 26

Gly Cys Pro Ser Leu Ala Glu His Trp Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetic construct

<400> SEQUENCE: 27

Val Phe Ala Asn Pro Glu Asp Cys Ala Phe Gly Lys
1               5                   10